United States Patent
Syud et al.

(10) Patent No.: US 10,159,760 B2
(45) Date of Patent: Dec. 25, 2018

(54) HER2 BINDERS

(71) Applicants: General Electric Company, Schenectady, NY (US); AFFIBODY AB, Solna (SE)

(72) Inventors: Faisal Ahmed Syud, Clifton Park, NY (US); Brian Duh-Lan Lee, Rexford, NY (US); Rong Zhang, Niskayuna, NY (US); Peter Brian Iveson, Amersham (GB); Paul Schaffer, Vancouver (CA); Tove Simonsson, Lund (SE); Elin Gunneriusson, Saltsjobaden (SE); Fredrik Frejd, Stockholm (SE); Lars Abrahmsen, Valhallavagen (SE); Joachim Feldwisch, Tyreso (SE); Nina Herne, Stockholm (SE); Christofer Lendel, Farsta (SE)

(73) Assignee: General Electric Company, Schenectady, NY (US)

( * ) Notice: Subject to any disclaimer, the term of this patent is extended or adjusted under 35 U.S.C. 154(b) by 136 days.

(21) Appl. No.: 15/083,424

(22) Filed: Mar. 29, 2016

(65) Prior Publication Data

US 2016/0199521 A1 Jul. 14, 2016

Related U.S. Application Data

(62) Division of application No. 12/975,425, filed on Dec. 22, 2010, now abandoned.

(51) Int. Cl.
*A61K 51/00* (2006.01)
*A61M 36/14* (2006.01)
*A61K 51/08* (2006.01)
*C07K 14/71* (2006.01)

(52) U.S. Cl.
CPC ........... *A61K 51/088* (2013.01); *C07K 14/71* (2013.01)

(58) Field of Classification Search
CPC ............... A61K 38/00; A61K 2121/00; A61K 2123/00; A61K 2300/00; A61K 38/08; A61K 38/10; A61K 38/16; A61K 49/00; A61K 49/0002; A61K 49/0004; A61K 49/12; A61K 49/14; A61K 51/00; A61K 51/06; A61K 51/08; A61K 51/088; A61K 51/10; C07K 14/71
USPC ........ 424/1.11, 1.65, 1.69, 9.1, 9.2, 9.3, 9.4, 424/9.5, 9.6; 514/1, 1.1, 19.2, 19.3, 19.4, 514/21.2, 21.3; 534/7, 10–16; 530/300, 530/324, 350
See application file for complete search history.

(56) References Cited

U.S. PATENT DOCUMENTS

| | | | | |
|---|---|---|---|---|
| 7,993,650 B2 * | 8/2011 | Carlsson | ................ | C07K 14/31 424/184.1 |
| 8,426,557 B2 * | 4/2013 | Bergman | ................ | C07K 14/65 530/324 |
| 8,501,909 B2 * | 8/2013 | Abrahmsen | ............ | A61K 51/08 424/9.1 |
| 8,883,120 B2 * | 11/2014 | Abrahmsen | ............ | A61K 51/08 424/1.69 |
| 9,061,080 B2 * | 6/2015 | Hiscock | ................ | C07K 14/71 |
| 9,175,067 B2 * | 11/2015 | Abrahmsen | ........ | B01D 15/3804 |
| 9,187,535 B2 * | 11/2015 | Lindborg | ............... | C07K 14/31 |
| 9,211,344 B2 * | 12/2015 | Ekblad | ................. | C07K 14/315 |
| 9,238,810 B2 * | 1/2016 | Jarstad | ................... | C07K 14/31 |
| 9,469,670 B2 * | 10/2016 | Abrahmsen | ............ | C07K 1/047 |

* cited by examiner

*Primary Examiner* — D. L. Jones
(74) *Attorney, Agent, or Firm* — GE Global Patent Operation; Pabitra K. Chakrabarti

(57) ABSTRACT

Imaging agents comprising an isolated polypeptide conjugated with a radionucleide and a chelator; wherein the isolated polypeptide binds specifically to HER2, or a variant thereof; and methods for preparing and using these imaging agents.

6 Claims, 21 Drawing Sheets

Specification includes a Sequence Listing.

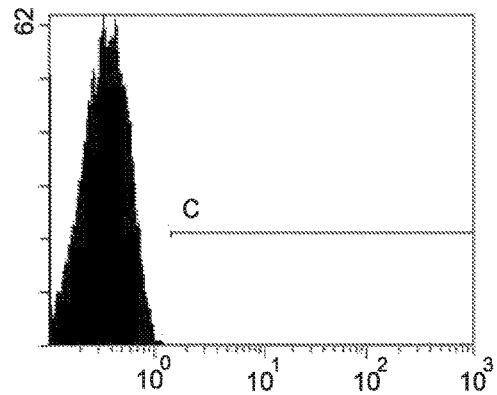
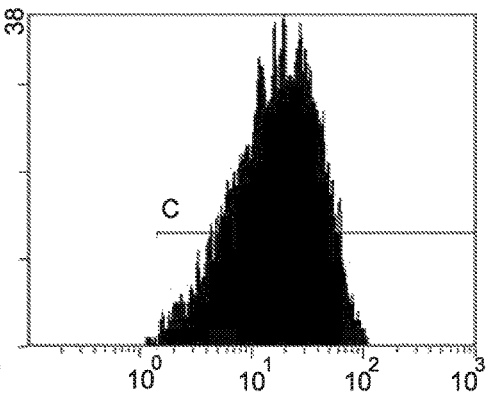
FIG. 2A          FIG. 2B
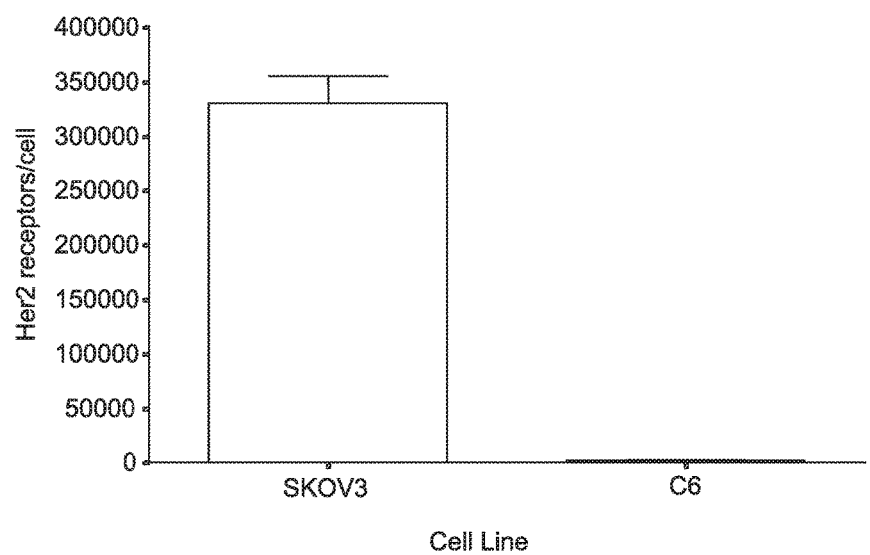
FIG. 2C

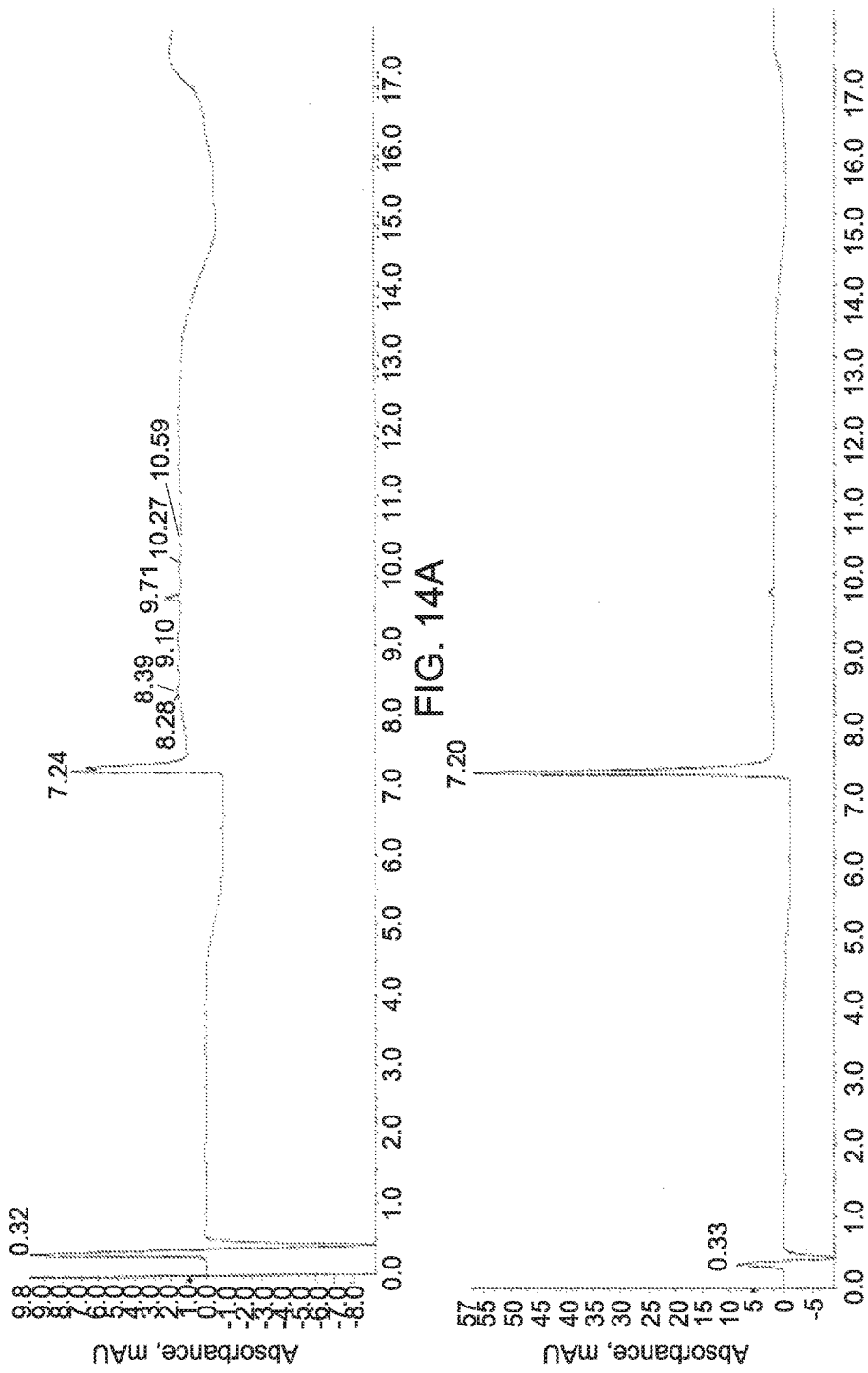

SEQUENCE LISTING

```
<160> NUMBER OF SEQ ID NOS: 7

<210> SEQ ID NO 1
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gly Ser Ser His His His His His Leu Gln Val Asp Asn Lys Phe
1               5                   10                  15

Asn Lys Glu Met Arg Asn Ala Tyr Trp Glu Ile Ala Leu Leu Pro Asn
            20                  25                  30

Leu Asn Asn Gln Gln Lys Arg Ala Phe Ile Arg Ser Leu Tyr Asp Asp
        35                  40                  45

Pro Ser Gln Ser Ala Asn Leu Leu Ala Glu Ala Lys Lys Leu Asn Asp
    50                  55                  60

Ala Gln Ala Pro Lys Val Asp Cys
65                  70
```

<210> SEQ ID NO 2
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Glu Ala Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
            20                  25                  30

Lys Leu Tyr Asp Asp Pro Ser Gln Ser Ser Glu Leu Leu Ser Glu Ala
        35                  40                  45

Lys Lys Leu Asn Asp Ser Gln Ala Pro Lys Val Asp Cys
    50                  55                  60

<210> SEQ ID NO 3
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Val Asp Asn Lys Phe Asn Lys Glu Met Arg Asn Ala Tyr Trp Glu Ile
1               5                   10                  15

Ala Leu Leu Pro Asn Leu Asn Val Ala Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys Val Asp Cys
    50                  55                  60

<210> SEQ ID NO 4
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Ser Ser His His His His His His Leu Gln Val Asp Asn Lys Phe
1               5                   10                  15

Asn Lys Glu Met Arg Asn Ala Tyr Trp Glu Ile Ala Leu Leu Pro Asn
            20                  25                  30

Leu Asn Val Ala Gln Lys Arg Ala Phe Ile Arg Ser Leu Tyr Asp Asp
        35                  40                  45

Pro Ser Gln Ser Ala Asn Leu Leu Ala Glu Ala Lys Lys Leu Asn Asp
    50                  55                  60

Ala Gln Ala Pro Lys Val Asp Cys
65                  70

<210> SEQ ID NO 5
<211> LENGTH: 130
<212> TYPE: PRT
<213> ORGANISM: Artificial Sequence
<220> FEATURE:

-continued

```
<223> OTHER INFORMATION: Description of Artificial Sequence: Synthetic
      polypeptide

<400> SEQUENCE: 5

Gly Ser Ser His His His His His Leu Gln Val Asp Asn Lys Phe
1               5                   10                  15

Asn Lys Glu Met Arg Asn Ala Tyr Trp Glu Ile Ala Leu Leu Pro Asn
            20                  25                  30

Leu Asn Val Ala Gln Lys Arg Ala Phe Ile Arg Ser Leu Tyr Asp Asp
            35                  40                  45

Pro Ser Gln Ser Ala Asn Leu Leu Ala Glu Ala Lys Lys Leu Asn Asp
    50                  55                  60

Ala Gln Ala Pro Lys Val Asp Asn Lys Phe Asn Lys Glu Met Arg Asn
65              70                  75                  80

Ala Tyr Trp Glu Ile Ala Leu Leu Pro Asn Leu Asn Val Ala Gln Lys
            85                  90                  95

Arg Ala Phe Ile Arg Ser Leu Tyr Asp Asp Pro Ser Gln Ser Ala Asn
            100                 105                 110

Leu Leu Ala Glu Ala Lys Lys Leu Asn Asp Ala Gln Ala Pro Lys Val
        115                 120                 125

Asp Cys
    130

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Gly Gly Gly
1

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5
```

HER2 BINDERS

CROSS-REFERENCE TO RELATED APPLICATIONS

This is a Divisional of U.S. patent application Ser. No. 12/975,425, which was filed on Dec. 22, 2010, and entitled HER2 BINDERS, which is hereby incorporated by reference in its entirely.

SEQUENCE LISTING

The instant application contains a Sequence Listing which has been submitted in ASCII format via EFS-Web and is hereby incorporated by reference in its entirety. Said ASCII copy, created on Mar. 29, 2016, is named 2355971-21.txt and is 4,860 bytes in size.

FIELD

The invention relates generally to imaging agents that bind to human epidermal growth factor receptor type 2 (HER2) and methods for making and using such agents.

BACKGROUND

Human epidermal growth factor receptor type 2 (HER2) is a transmembrane protein and a member of erbB family of receptor tyrosine kinase proteins. HER2 is a well-established tumor biomarker that is over-expressed in a wide variety of cancers, including breast, ovarian, lung, gastric, and oral cancers. Therefore, HER2 has great value as a molecular target and as a diagnostic or prognostic indicator of patient survival, or a predictive marker of the response to antineoplastic surgery.

Over the last decade, noninvasive molecular imaging of HER2 expression using various imaging modalities has been extensively studied. These modalities include radionuclide imaging with Positron Emission Tomography (PET) and Single Photon Emission Tomography (SPECT). PET and SPECT imaging of HER2 (HER2-PET and HER2-SPECT, respectively) provide high sensitivity, high spatial resolution. PET imaging of HER2 also provides strong quantification ability. HER2-PET and HER2-SPECT are particularly useful in real-time assays of overall tumor HER2 expression in patients, identification of HER2 expression in tumors over time, selection of patients for HER-targeted treatment (e.g., trastuzumab-based therapy), prediction of response to therapy, evaluation of drug efficacy, and many other applications. However, no PET or SPECT-labeled HER2 ligands have been developed that have a chemistry and exhibit in vivo behaviors which would be suitable for clinical applications.

Naturally occurring Staphylococcal protein A comprises domains that form a three-helix structure (a scaffold) that binds to the fragment, crystallizable region (Fc) of immunoglobulin isotype G (IgG). Certain polypeptides, derived from the Z-domain of protein A, contain a scaffold composed of three α-helices connected by loops. Certain amino acid residues situated on two of these helices constitute the binding site for the Fc region of IgG. Alternative binder molecules have been prepared by substituting surface-exposed amino acid residues (13 residues) situated on helices 1 and 2, to alter the binding ability of these molecules. One such example is HER2 binding molecules or HER2 binders. These HER2 binders have been labeled with PET or SPECT-active radionuclides. Such PET and SPECT-labeled binders provide the ability to measure in vivo HER2 expression patterns in patients and would therefore aid clinicians and researchers in diagnosing, prognosing, and treating HER2-associated disease conditions.

HER2 binding affibody molecules, radiolabeled with the PET-active radionucleide, $^{18}F$, have been evaluated as imaging agents for malignant tumors that over express HER2. HER2 binding Affibody molecules, conjugated with $^{99m}Tc$ via the chelators such as maGGG (mercaptoacetyltriglycyl), CGG (cysteine-diglycyl), CGGG (SEQ ID NO: 6) (cysteine-triglycyl) or AA3, have also been used for diagnostic imaging. The binding of these molecules to target HER2 expressing tumors has been demonstrated in mice.

In most of the cases, the signal-generating $^{18}F$ group is introduced to the Affibody through a thiol-reactive maleimide group. The thiol reactive maleimide group is prepared using a multi-step synthesis after $^{18}F$ incorporation. However, this chemistry only provides a low radiochemical yield. Similarly, the conjugation of $^{99m}Tc$ with the Affibody is a multistep, low yield, process. In addition, Tc reduction and the complex formation with chelates, require high pH (e.g., pH=11) conditions and long reaction times.

Though the in vivo performance of $^{18}F$ labeled Affibody molecules was moderately good, there is significant room for improvement. For example, in some studies, the tumor uptake was found to be only 6.36±1.26% ID/g 2 hours post-injection of the imaging agent. On the other hand, $^{99m}Tc$ labeled Affibody molecules have predominant hepatobiliary clearance, which causes a high radioactivity accumulation in the intestine, which restricts its use for detecting HER2 tumors and metastates in the abdominal area.

Therefore, there is a need for chemistries and methods for synthesizing radiolabeled polypeptides in which the radioactive moiety, such as $^{18}F$ can be introduced at the final stage, which in turn will provide high radiochemical yields. In addition, there is a need for a new HER2 based imaging agent for PET or SPECT imaging with improved properties particularly related to renal clearance and toxicity effects.

BRIEF DESCRIPTION

The compositions of the invention are a new class of imaging agents that are capable of binding specifically to HER2 or variants thereof.

In one or more embodiments, the imaging agent composition comprises an isolated polypeptide comprising SEQ. ID No. 1, SEQ. ID. No 2 or a conservative variant thereof, conjugated with a $^{99m}Tc$ via a diaminedioxime chelator. The diaminedioxime chelator may comprise Pn216, cPn216, Pn44, or derivatives thereof. The isolated polypeptide binds specifically to HER2 or variants thereof.

In one or more embodiments, the imaging agent composition comprises an isolated polypeptide comprising SEQ. ID No. 1, SEQ. ID. No 2 or a conservative variant thereof, conjugated with $^{67}Ga$ or $^{68}Ga$ via a NOTA chelator. The isolated polypeptide binds specifically to HER2 or variants thereof.

In one or more embodiments, the imaging agent composition comprises an isolated polypeptide comprising SEQ. ID No. 1, SEQ. ID. No 2 or a conservative variant thereof, conjugated with $^{18}F$ via a linker. The linker comprises a group derived from an aminoxy group, an azido group, or an alkyne group. The isolated polypeptide binds specifically to HER2 or variants thereof.

An example of the methods of the invention, for preparing an imaging agent composition, comprises (i) providing an isolated polypeptide comprising SEQ. ID No. 1, SEQ. ID No. 2 or a conservative variant thereof; and (ii) reacting a diaminedioxime chelator with the polypeptide to form a chelator conjugated polypeptide. In another example, the method comprises (i) providing an isolated polypeptide comprising SEQ. ID No. 1, SEQ. ID No. 2 or a conservative variant thereof; (ii) reacting the polypeptide with a linker; and (iii) reacting the linker with an $^{18}$F moiety to form a $^{18}$F conjugated polypeptide. The linker may comprise an aminoxy group, an azido group, or an alkyne group.

BRIEF DESCRIPTION OF THE DRAWINGS

These and other features, aspects, and advantages of the present invention will become better understood when the following detailed description is read with reference to the accompanying figures wherein:

FIG. 2A and FIG. 2B are graphs of the qualitative flow cytometry of C6 (rat glioma, control) and human anti-HER2 antibody to SKOV3 (human ovarian carcinoma) respectively. FIG. 2C shows a bar chart for Her2 receptors per cell for SKOV3 and C6 cell lines.

FIG. 14A is the reverse phase HPLC chromatogram of Z00342 (SEQ. ID No. 1) starting material and 14B is the reverse phase HPLC chromatogram of the purified Z00342 (SEQ. ID No. 1)-AO imaging agent composition, both analyzed at 280 nm.

DETAILED DESCRIPTION

Figure 1A:
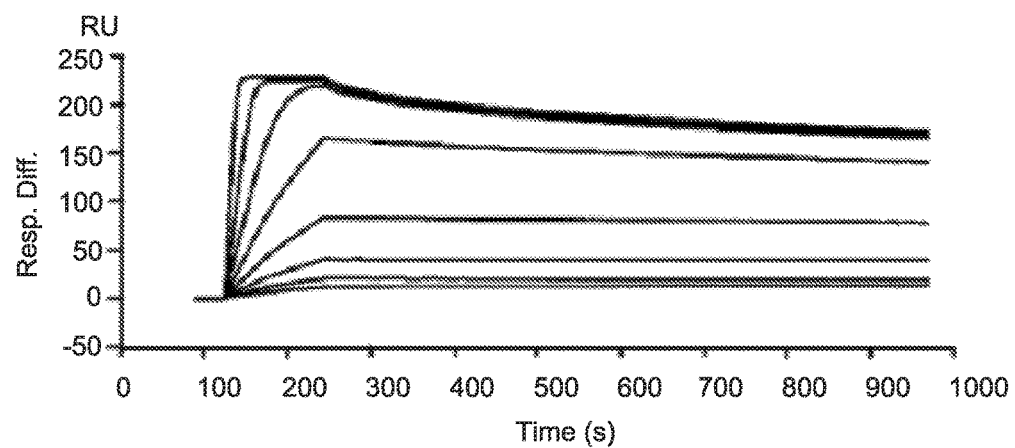
FIGS. 1A and 1B are graphs of the surface plasmon resonance (SPR) of the binding affinity of two anti-HER2 polypeptides, Z477 (SEQ. ID No. 3) and (Z477)$_2$ (SEQ. ID No. 5), respectively, at eight different concentrations, to human HER2.

The imaging agents of the invention generally comprise an isolated polypeptide of SEQ. ID No. 1, SEQ. ID No. 2 or a conservative variant thereof, conjugated with $^{18}$F, $^{99m}$Tc, $^{67}$Ga or $^{68}$Ga; and methods for making and using the compositions. The isolated polypeptide binds specifically to HER2 or its variant thereof. In one or more embodiments, the sequence of the isolated polypeptide has at least 90% sequence similarity to any of SEQ. ID No. 1, SEQ. ID No. 2 or conservative variant thereof.

The isolated polypeptide may comprise natural amino acids, synthetic amino acids, or amino acid mimetics that function in a manner similar to the naturally occurring amino acids. Naturally occurring amino acids are those encoded by the genetic code, as well as those amino acids that are later modified, for example, hydroxyproline, α-carboxyglutamate, O-phosphoserine, phosphothreonine, and phosphotyrosine.

The isolated polypeptides may be prepared using standard solid phase synthesis techniques. Alternatively, the polypeptides may be prepared using recombinant techniques. When the polypeptides are prepared using recombinant techniques, the DNA encoding the polypeptides or conservative variants thereof may be isolated. The DNA encoding the polypeptides or conservative variants thereof may be inserted into a cloning vector, introduced into a host cell (e.g., a eukaryotic cell, a plant cell, or a prokaryotic cell), and expressed using any art recognized expression system.

The polypeptide may be substantially comprised of a single chiral form of amino acid residues. Thus, polypeptides of the invention may be substantially comprised of either L-amino acids or D-amino acids; although a combination of L-amino acids and D-amino acids may also be employed.

As the polypeptides provided herein are derived from the Z-domain of protein A, residues on the binding interface may be non-conservatively substituted or conservatively substituted while preserving binding activity. In some embodiments, the substituted residues may be derived from any of the 20 naturally occurring amino acids or any analog thereof.

The polypeptides may be about 49 residues to about 130 residues in length. The specific polypeptide sequences are listed in Table 1.

TABLE 1

| Name | Sequence | Length |
|---|---|---|
| Z00342 (SEQ. ID No. 1) | GSSHHHHHHLQVDNKFNKEMRNA YWEIALLPNLNNQQKRAFIRSLYDD PSQSANLLAEAKKLNDAQAPKVDC | 72 |
| Z02891 (SEQ. ID No. 2) | AEAKYAKEMRNAYWEIALLPNLTN QQKRAFIRKLYDDPSQSSELLSEAK KLNDSQAPKVDC | 61 |
| Z00477 (SEQ. ID No. 3) | VDNKFNKEMRNAYWEIALLPNLNV AQKRAFIRSLYDDPSQSANLLAEAK KLNDAQAPKVDC | 61 |
| Z00477-His6 (SEQ. ID No. 4)('His6' disclosed as SEQ ID NO: 7) | GSSHHHHHHLQVDNKFNKEMRNA YWEIALLPNLNVAQKRAFIRSLYDD PSQSANLLAEAKKLNDAQAPKVDC | 72 |
| (Z00477)$_2$ (SEQ. ID No. 5) | GSSHHHHHHLQVDNKFNKEMRNA YWEIALLPNLNVAQKRAFIRSLYDD PSQSANLLAEAKKLNDAQAPKVDN KFNKEMRNAYWEIALLPNLNVAQK RAFIRSLYDDPSQSANLLAEAKKLN DAQAPKVDC | 130 |

Additional sequences may be added to the termini to impart selected functionality. Thus, additional sequences may be appended to one or both termini to facilitate purification or isolation of the polypeptide, alone or coupled to a binding target (e.g., by appending a His tag to the polypeptide).

The polypeptides listed in Table 1 may be conjugated with $^{18}$F via a linker; $^{99m}$Tc via a diaminedioxime chelator, or with $^{67}$Ga or $^{68}$Ga via a NOTA chelator. Table 2 provides the isoelectric point (pI), of these polypeptides.

TABLE 2

| | pI | MW (kD) |
|---|---|---|
| His6-Z00477 (SEQ. ID No. 4) ('His6' disclosed as SEQ ID NO: 7) | 8.31 | 8143.11 |
| Z02891(SEQ. ID No. 2) | 8.10 | 7029.96 |
| His6-Z00342 ('His6' disclosed as SEQ ID NO: 7) | 8.14 | 8318.27 |

In one or more embodiments, the isolated polypeptide, comprising SEQ. ID No. 1, SEQ. ID No. 2 or a conservative variant thereof, may be conjugated with $^{18}$F. The $^{18}$F may be incorporated at a C terminus, at a N-terminus, or at an internal position of the isolated polypeptide.

In one or more embodiments, the $^{18}$F may be conjugated to the isolated polypeptide via a linker. The linker may comprise, an aminoxy group, an azido group, or an alkyne group. The aminoxy group of the linker may be attached with an aldehyde, such as a fluorine-substituted aldehyde. An azide group of the linker may be attached with a fluorine substituted alkyne. Similarly, an alkyne group of the linker may be attached with a fluorine substituted azide. The linker may also comprise a thiol reactive group. The linker may comprise of a maleimido-aminoxy, maleimido-alkyne or maleimido-azide group. The $^{18}$F conjugated polypeptide may be prepared by: (i) providing the isolated polypeptide comprising SEQ. ID No. 1, SEQ. ID No. 2, or a conservative variant thereof; (ii) reacting the polypeptide with a linker, wherein the linker comprises an aminoxy group, an azido group, or an alkyne group, to form a linker conjugated polypeptide; and reacting the linker with an $^{18}$F moiety.

In another embodiment, the method may comprise: (i) providing an isolated polypeptide comprising SEQ. ID No. 1, SEQ. ID No. 2, or a conservative variant thereof; (ii) providing a linker; (iii) reacting the linker with the $^{18}$F moiety to form a $^{18}$F labeled linker; and (iv) reacting the $^{18}$F labeled linker with the isolated polypeptide of SEQ. ID No 1, SEQ ID no 2, or a conservative variant thereof, to form a linker conjugated polypeptide.

Using the above-described examples, fluorine or radio-fluorine atom(s), such as $^{18}$F, may be introduced onto the polypeptides. A fluorine-substituted polypeptide results when a fluorine-substituted aldehyde is reacted with the aminoxy group of the linker conjugated polypeptide. Similarly, a fluorine substituted polypeptide results, when a fluorine substituted azide or alkyne group is reacted with the respective alkyne or azide group of the linker conjugated polypeptide. A radiofluorine-labeled polypeptide or imaging agent composition results, when a radiofluorine-substituted aldehyde, azide or alkyne is reacted with the respective aminoxy, alkyne or azide group of the linker conjugated polypeptide. Further, each of the aldehydes, azides or alkynes may have a radiofluorine ($^{18}$F) substituent, to prepare radiofluorine-labeled imaging agent compositions. The methods for introducing fluorine onto the polypeptide may also be used to prepare a fluorinated imaging agent composition of any length. Thus, in some embodiments the polypeptide of the imaging agent composition may comprise, for example, 40 to 130 amino acid residues.

The chemistry for the synthesizing linker-conjugated polypeptide of the imaging agents is facile, and the one step reaction of the methods are more efficient than previously known methods and result in higher yields. The methods are easier to carry out, faster and are performed under milder, more user friendly, conditions. For example, the method for labeling a polypeptide with $^{18}$F conjugated with a linker (e.g., 18F-fluorobenzaldehyde) is simpler than the procedures known in the art. $^{18}$F conjugated-linker is prepared in one step by the direct nucleophilic incorporation of $^{18}$F onto the trimethylanilinium precursor. $^{18}$F-linker (i.e., $^{18}$F-FBA) is then conjugated to the polypeptide, such as an affibody. The preparation of the linker is also easier than previously known methods in the art. Moreover, radiolabeled aminoxy based linker-conjugated polypeptides, and the cPn family of chelator conjugated polypeptides (e.g., affibody), show significantly better biodistribution and better tumor uptake, as well as better clearance with less liver uptake.

The fluorine-labeled compositions are highly desired materials in diagnostic applications. $^{18}$F labeled imaging agent compositions may be visualized using established imaging techniques such as PET.

In another embodiment, the polypeptide may be conjugated with $^{99m}$Tc via a diamindioxime chelator of formula (1).

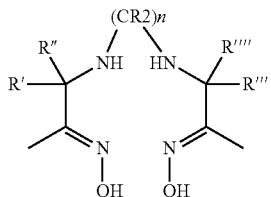

wherein R', R'', R''', R'''' is independently H or $C_{1-10}$ alkyl, $C_3$-10 alkylary, $C_{2-10}$ alkoxyalkyl, $C_{1-10}$ hydroxyalkyl, $C_{1-10}$ alkylamine, $C_{1-10}$ fluoroalkyl, or 2 or more R groups, together with the atoms to which they are attached to form a carbocyclic, heterocyclic, saturated or unsaturated ring, wherein R may be H, $C_{1-10}$ alkyl, $C_{3-10}$ alkylary, $C_{2-10}$ alkoxyalkyl, $C_{1-10}$ hydroxyalkyl, $C_{1-10}$ alkylamine, or $C_{1-10}$ fluoroalkyl. In one embodiment, n may vary from 0-5. Examples of methods for preparing diaminedioxime chelators are described in PCT Application, International Publication No. WO2004080492(A1) entitled "Methods of radio fluorination of biologically active vector", and PCT Application, International Publication No. WO2006067376(A2) entitled "Radio labelled conjugates of RGD-containing peptides and methods for their preparation via click-chemistry", which are incorporated herein by references.

The $^{99m}$Tc may be conjugated to the isolated polypeptide via the diamindioxime at the N-terminus of the isolated polypeptide. The chelator may be a bifunctional compound. In one embodiment, the bifunctional compound may be Mal-cPN216. The Mal-cPN216 comprises a thiol-reactive maleimide group for conjugation to a terminal cysteine of the polypeptide of SEQ ID No. 1 or SEQ ID No 2 and a bis-amineoxime group (diamindioxime chelator) for chelating with $^{99m}$Tc. The Mal-cPN216 may have a formula (2).

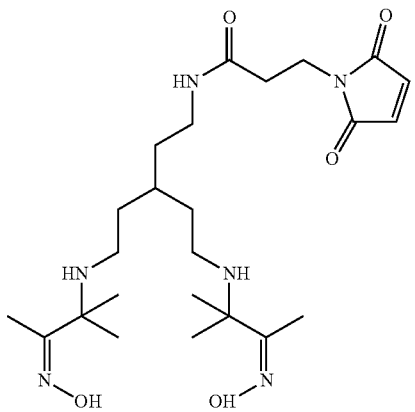 [SMILES: C/C(=N/O)C(C)(C)NCCC(CCNC(=O)CCN1C(=O)C=CC1=O)CCNC(C)(C)/C(C)=N\O]

The diamindioxime chelator conjugated peptide may be prepared by (i) providing an isolated polypeptide comprising SEQ. ID No. 1, SEQ. ID No. 2 or a conservative variant thereof, (ii) reacting a diamindioxime chelator with the polypeptide to form the diamindioxime conjugated polypeptide. The diamindioxime chelator may be further conjugated with $^{99m}$Tc.

In one or more embodiments, the polypeptide may be conjugated with $^{67}$Ga, or $^{68}$Ga via NOTA (1,4,7-triazacyclononane-N,N',N''-triacetic acid) chelator. The NOTA conjugated polypeptide may be prepared by (i) providing an isolated polypeptide comprising SEQ. ID No. 1, SEQ. ID No. 2 or a conservative variant thereof, (ii) reacting a NOTA chelator with the polypeptide to form the NOTA conjugated polypeptide. The NOTA chelator may be further conjugated with $^{67}$Ga or $^{68}$Ga.

In one embodiment, the Ga, specifically $^{67}$Ga, may be conjugated to the isolated polypeptide via NOTA chelator. The NOTA chelator may be functionalized with a maleimido group, as described in formula (3).

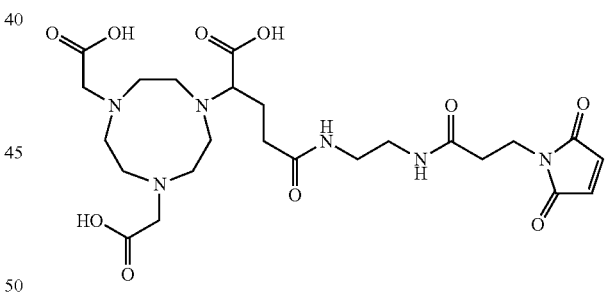

The invention also comprises methods of imaging at least a portion of a subject. In one embodiment, the method comprises administering the imaging agent composition to the subject and imaging the subject. The subject may be imaged, for example, with a diagnostic device.

The method may further comprise the steps of monitoring the delivery of the composition to the subject and diagnosing the subject with a HER2-associated disease condition (e.g., breast cancer). In one embodiment, the subject may be a mammal, for example, a human. In another embodiment, the subject may comprise cells or tissues. The tissues may be used in biopsy. The diagnostic device may employ an imaging method chosen from magnetic resonance imaging, optical imaging, optical coherence tomography, X-ray, computed tomography, positron emission tomography, or combinations thereof.

The imaging agent compositions may be administered to humans and other animals parenterally. Pharmaceutical compositions of this invention for parenteral injection comprise pharmaceutically-acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by using coating materials such as lecithin, by adjusting the particle size in dispersions, and by using surfactants.

These imaging agent compositions may also contain adjuvant such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents, which delay absorption such as aluminum monostearate and gelatin.

The imaging agent compositions may be dispersed in physiologically acceptable carrier to minimize potential toxicity. Thus, the imaging agents may be dispersed in a biocompatible solution with a pH of about 6 to about 8. In some embodiments, the agent is dispersed in a biocompatible solution with a pH of about 7 to about 7.4. In other embodiments, the agent is dispersed in a biocompatible solution with a pH of about 7.4.

The imaging agent compositions may be combined with other additives that are commonly used in the pharmaceutical industry to suspend or dissolve the compounds in an aqueous medium, and then the suspension or solution may be sterilized by techniques known in the art. The imaging agent composition may be administered in a variety of forms and adapted to the chosen route of administration. For example, the agents may be administered topically (i.e., via tissue or mucus membranes), intravenously, intramuscularly, intradermally, or subcutaneously. Forms suitable for injection include sterile aqueous solutions or dispersions and sterile powders for the preparation of sterile injectable solutions, dispersions, liposomal, or emulsion formulations. Forms suitable for inhalation use include agents such as those dispersed in an aerosol. Forms suitable for topical administration include creams, lotions, ointments, and the like.

The imaging agent compositions may be concentrated to conveniently deliver a preferred amount of the agents to a subject and packaged in a container in the desired form. The agent may be dispensed in a container in which it is dispersed in a physiologically acceptable solution that conveniently facilitates administering the agent in concentrations between 0.1 mg and 50 mg of the agent per kg body weight of the subject.

In one or more embodiments, the target tissue may be imaged about four hours after administering the agents. In alternative embodiments, the target tissue may be imaged about 24 hours after administering the agents to the subject.

Examples

The following examples are provided for illustration only and should not be construed as limiting the invention.

A panel of tumorigenic cell lines with a reasonable probability of expressing HER2 was selected based on available literature (Bruskin, et. al. Nucl. Med. Biol. 2004: 31: 205; Tran, et. al. Imaging agent composition Chem. 2007: 18: 1956), as described in Table3.

TABLE 3

| Cell line | Species | Type | Purpose |
| --- | --- | --- | --- |
| SKOV3 | Human | Ovarian carcinoma | Candidate |
| SKBR3 | Human | Breast carcinoma | Candidate |
| C6 | Rat | Glioma | control |

All cell lines were obtained from the American Type Culture Collection (ATCC) and cultured as recommended. Cells were cultured to >90% confluence prior to use. Flow cytometry (Beckman Coulter Cytomics FC500 MPL) was carried out on the cell lines listed in table 4 using anti-Her2 primary antibodies (R&D Systems, PN MAB 1129) and the Dako QIFIKIT (PN K0078) for quantitative analysis of indirect immunofluorescence staining Calibration beads with 5 different populations bearing different numbers of Mab molecules were used in conjunction with the cell lines to determine number of surface receptors per cell. In all cases, appropriate isotype controls were obtained from the corresponding vendors.

Adherent cells were released from their flasks using cell dissociation buffer (PBS+10 mM EDTA) rather than trypsin to avoid proteolysis of cell surface receptors. Cells were washed twice in PBS and resuspended in ice-cold FC buffer (PBS+0.5% BSA w/v) to a concentration of 5-10×10$^6$ cells/ml. 100 µL aliquots of cells were mixed with 5 µg of primary antibody and incubated, on ice, for 45 minutes. Cells were then washed with 1 ml of ice cold flow cytometry (FC) buffer (PBS with 2% bovine serum albumin), centrifuged at 300×g for 5 min, and resuspended in 0.5 µL of FC buffer. 100 µL of 1:50 dilution with PBS of the secondary antibody fragment (F(ab)$_2$ FITC-conjugated goat anti-mouse Immunoglobulins) was added and incubated, on ice and in the dark, for 45 minutes. Cells were then washed twice with 1 mL of ice cold FC buffer, centrifuged at 300×g for 5 min, and resuspended in 500 µL of FC buffer. All stained cells were passed through a 100-micron filter prior to flow cytometry to prevent clogs of the flow cell.

Flow cytometry was carried out on a Beckman Coulter Cytomics FC500 MPL. A minimum of 5×10$^4$ events was collected for each tube. All analyses were single color, with detection of FITC in FL1. Forward scatter (FS) and side scatter (SS) data demonstrated that all cell populations were tightly grouped.

Figure 3:
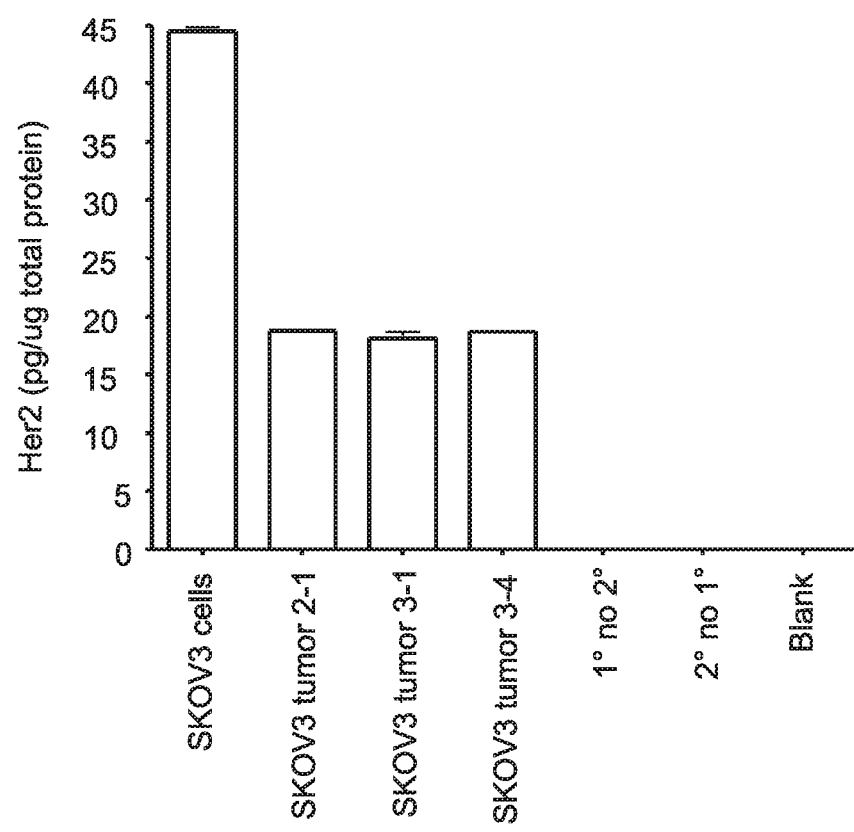
FIG. 3 is a bar graph of ELISA assays for Her2 with respect to a panel of tumor types SKOV3 2-1, SKOV3 3-1, SKOV3 3-4, with respect to SKOV3 cells, and blank.

Flow cytometry was used to evaluate the cells for their HER2 expression in vitro (FIGS. 2A, 2B, and 2C) with SKOV3 cells showing the highest level of HER2 expression (FIG. 3). The results in FIG. 3 were reproducible (n=3).

The highest expressing cell line was SKOV3. These cells were injected into 6-12 week old immuno-compromised mice and allowed to grow tumors. Tumor growth curves and success rates were dependent on the number of cells inoculated. Optimal tumor growth was obtained with three to four million cells/mouse In vivo studies were carried out with female CD-1 nude mice (Charles River Labs, Hopkinton, Mass.) with an age range between 6 and 15 weeks. Mice were housed in a ventilated rack with food and water ad libitum and a standard 12 hour day-night lighting cycle. For xenografts, animals were injected with 100 µl of cells in PBS. Cells were implanted subcutaneously in the right hindquarter. Implantation was performed under isoflurane anesthesia. For SKOV3, between $3 \times 10^6$ to $4 \times 10^6$ cells were implanted in each mouse. Under these conditions, useable tumors (100 to 300 μg) were obtained in 3 to 4 weeks in greater than 80% of animals injected.

Tumors were collected from mice by dissection, and whole tumors were stored at −20° C. until processing. Tumors were ground on ice in 1 ml of RIPA buffer supplemented with a protease inhibitor cocktail (Santa Cruz Biotech, Santa Cruz, Calif. #24948) in a Dounce homogenizer. Homogenates were then incubated on ice for 30 minutes, then centrifuged at 10,000×G for 10 minutes in a refrigerated centrifuge. Supernatants were collected and stored on ice or at 4° C. until further processing. Protein concentrations in lysates were determined using a BCA protein assay kit (Pierce Biotechnology 23225). Lysates were diluted to a standard concentration to yield 20 μg of protein/well in the microtiter plate. ELISA's were run with a commercially available human HER2 kit (R&D Systems, DYC1129) according to the manufacturer's instructions. Each sample was run in triplicate, and data are reported as pg HER2/μg total protein, errors are reported as standard deviations.

Target expression in vivo was measured by ELISA. Excised tumors were homogenized and analyzed for HER2 using a commercially available matched pair kit (R&D systems, DYC1129, Minneapolis, Minn.). The results, in FIG. 3, show that the SKOV3 cell line grows a high-expressing tumor. ELISA controls were cell-culture lysates of the negative control lines used for flow cytometry. These results indicate that tumor xenografts of SKOV3 are appropriate for the in vivo study of molecules targeting human HER2.

All polypeptides were received from Affibody AB in Sweden. The polypeptides are referred to by their numeric internal development codes, which are prefixed with "Z". Table 1 details the polypeptides described herein. The polypeptides include polypeptide Z00342 (SEQ. ID No. 1); polypeptide Z02891 (SEQ. ID No. 2); polypeptide Z00477 (SEQ. ID No. 3 and 4), and dimer of Z00477, i.e., $(Z00477)_2$ (SEQ. ID No. 5).

Binding interactions between the polypeptids and the HER2/neu antigen were measured in vitro using surface plasmon resonance (SPR) detection on a Biacore™ 3000 instrument (GE Healthcare, Piscataway, N.J.). The extracellular domain of the Her2/neu antigen was obtained as a conjugate with the Fc region of human IgG (Fc-Her2) from R&D Systems (Minneapolis, Minn.) and covalently attached to a CM-5 dextran-functionalized sensor chip (GE Healthcare, Piscataway, N.J.) pre-equilibrated with HBS-EP buffer (0.01M HEPES pH 7.4, 0.15M NaCl, 3 mM EDTA, 0.005% v/v surfactant P20) at 10 μL/min and subsequently activated with EDC and NHS. The Fc-HER2 (5 μg/ml) in 10 mM sodium acetate (pH 5.5) was injected onto the activated sensor chip until the desired immobilization level (~3000 Resonance Units) was achieved (2 min). Residual activated groups on the sensor chip were blocked by injection of ethanolamine (1 M, pH 8.5). Any non-covalently bound conjugate was removed by repeated (5×) washing with 2.5 M NaCl, 50 mM NaOH. A second flow cell on the same sensor chip was treated identically, except with no Fc-HER2 immobilization, in order to serve as a control surface for refractive index changes and non-specific binding interactions with the sensor chip. Prior to the kinetic study, binding of the target analyte was tested on both surfaces and a surface stability experiment was performed to ensure adequate removal of the bound analyte and regeneration of the sensor chip following treatment with 2.5 M NaCl, 50 mM NaOH. SPR sensorgrams were analyzed using the BIAevaluation software (GE Healthcare, Piscataway, N.J.). The robustness of the kinetic model was determined by evaluation of the residuals and standard error for each of the calculated kinetic parameters, the "goodness of the fit" ($\chi_2$<10), and a direct comparison of the modeled sensorgrams to the experimental data. SPR measurements were collected at eight analyte concentrations (0-100 nM protein) and the resulting sensorgrams were fitted to a 1:1 Langmuir binding model.

Figure 1B:
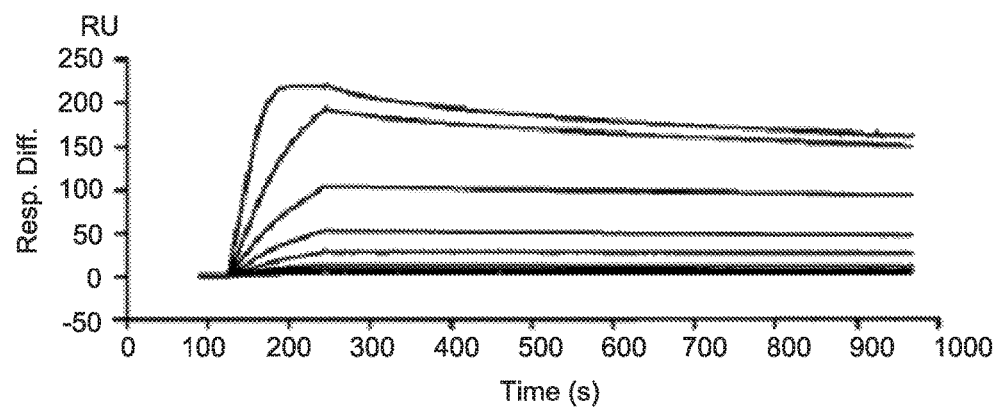

FIG. 1 shows example surface plasmon resonance (SPR) data obtained for Z00477 (SEQ. ID No. 3) and $(Z00477)_2$ (SEQ. ID No. 5) when run on human HER2-functionalized surfaces. This relationship holds true for all polypeptides for which the affinities are known (Table 2), in which the values for the dimer Z(477)2 (SEQ. ID No. 5) are estimates based on avidity affect.

Labeling of His6 (SEQ ID NO: 7)-tagged Polypeptides with the fac-$[^{99m}Tc(CO)_3]^+$ core was accomplished using modifications to a previously published procedure (Waibel, R.; et al., A. Nat. Biotechnol. 1999, 17, 897.). Briefly, Na[$^{99m}TcO_4$] in saline (4 mCi, 2 mL) was added to an Isolink® boranocarbonate kit (Alberto, R. et al, J. Am. Chem. Soc. 2001, 123, 3135.). The resulting solution was heated to 95° C. for 15-20 minutes, to give fac-$[^{99m}Tc(CO)_3(H_2O)_3]^+$. A portion (2 mCi, 1 mL) of the solution was removed and neutralized to pH ~7 with 1 N HCl. A 325 μL aliquot was removed and added to a solution of the His6-Polypeptide (SEQ ID NO: 7) (40 μg). The resulting solution was heated in a water bath at 35-37° C. for 40 minutes. Typical radiochemical yields ranged from 80-95% (determined by ITLC-SG, Biodex, 0.9% NaCl). The crude reaction products were chromatographed on a NAP-5 column (GE Healthcare, 10 mM PBS) to give products of >99% radiochemical purity. Typical specific activities obtained were 3-4 μCi/μg. The resulting solution was then diluted with 10 mM PBS to give the proper concentration for subsequent biodistribution studies.

HPLC was carried out on an Agilent 1100 series HPLC equipped with a Grace-Vydac Peptide/Protein C4 (4.6×250 mm) column and a Raytest GABI radioactivity detector. Solvent A was 95:5 water:MeCN with 0.1% TFA, and solvent B was 5:95 water:MeCN with 0.1% TFA. The gradient was as follows (all changes linear; time/% B): 0/0, 4/20, 16/60, 20/100, 25/100, 26/0, 31/0.

Each polypeptide was labeled with the tricarbonyltechnetium core in high yield (>90%) before purification. Purification by NAP-5 chromatography gave samples of $^{99m}$Tc-labeled Polypeptides in >99% radiochemical purity (Table 4)

TABLE 4

| Compound | Grade yield (%) | Isolated yield (decay corr.) (%) | NAP-5 RCP (%) |
|---|---|---|---|
| Z00477 (SEQ. ID No. 3) | 56.9 | 24.7 (26.9) | 99.5 |

Figure 4:
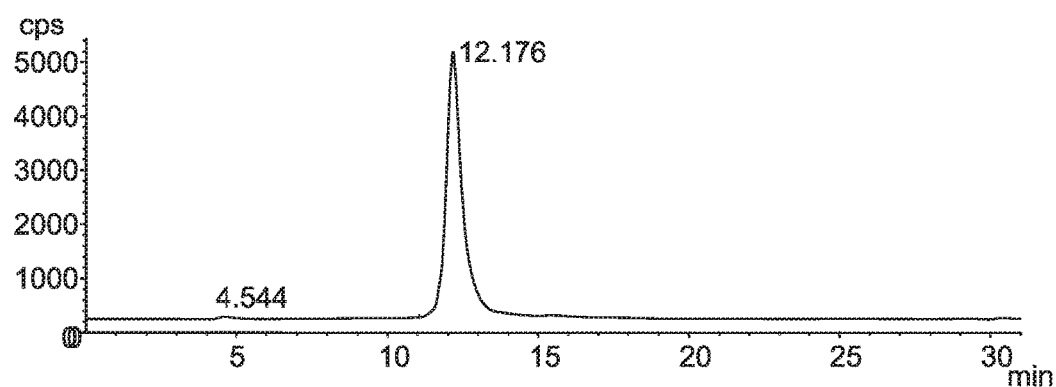
FIG. 4 is a reverse phase HPLC gamma chromatogram of $^{99m}$Tc labeled Z00477 (SEQ. ID No. 3).

Representative HPLC chromatograms of NAP-5 purified radiolabeled polypeptides are shown in FIG. 4. The retention time of the radiolabeled species was virtually unchanged from the corresponding unlabeled polypeptide's retention time in a 220 nm UV chromatogram (except for the time difference due to the physical separation of the UV and gamma detectors; data not shown).

Animal Models used to study $^{99m}$Tc(CO)$_3$(His$_6$)-Polypeptides ('His$_6$' disclosed as SEQ ID NO: 7)

In vivo studies were carried out with female CD-1 nude mice (Charles River Labs, Hopkinton, Mass.) with an age range between 6 and 15 weeks. Mice were housed in a ventilated rack with food and water ad libitum and a standard 12 hour day-night lighting cycle. For xenografts, animals were injected with 100 μl of cells in PBS. Cells were implanted subcutaneously in the right hindquarter. Implantation was performed under isoflurane anesthesia. For SKOV3, between 3×10$^6$ to 4×10$^6$ cells were implanted in each mouse. Under these conditions, useable tumors (100 to 300 μg) were obtained in 3 to 4 weeks in greater than 80% of animals injected.

Biodistribution

Mice were given tail-vein injections of ~1 μg of $^{99m}$Tc-labeled polypeptides (~3 μCi/1 μg). Mice were placed in filter-paper lined cages until euthanasia. Three mice were euthanized at each timepoint and tissues of interest dissected and counted on a Perkin Elmer Wallac Wizard 1480 Gamma Counter. Data were collected for blood, kidney, liver, spleen, and injection site (tail). Urine from cages was pooled with the bladder and also counted. The remaining tissues were counted and the sum of all tissues plus urine for each animal was summed to provide the total injected dose. The % injected dose for each organ was determined based on this total, and organs were weighed for determination of the % injected dose per gram, (% ID/g). Data is reported as mean value for all three mice in the timepoint with error bars representing the standard deviation of the group.

Figure 6:
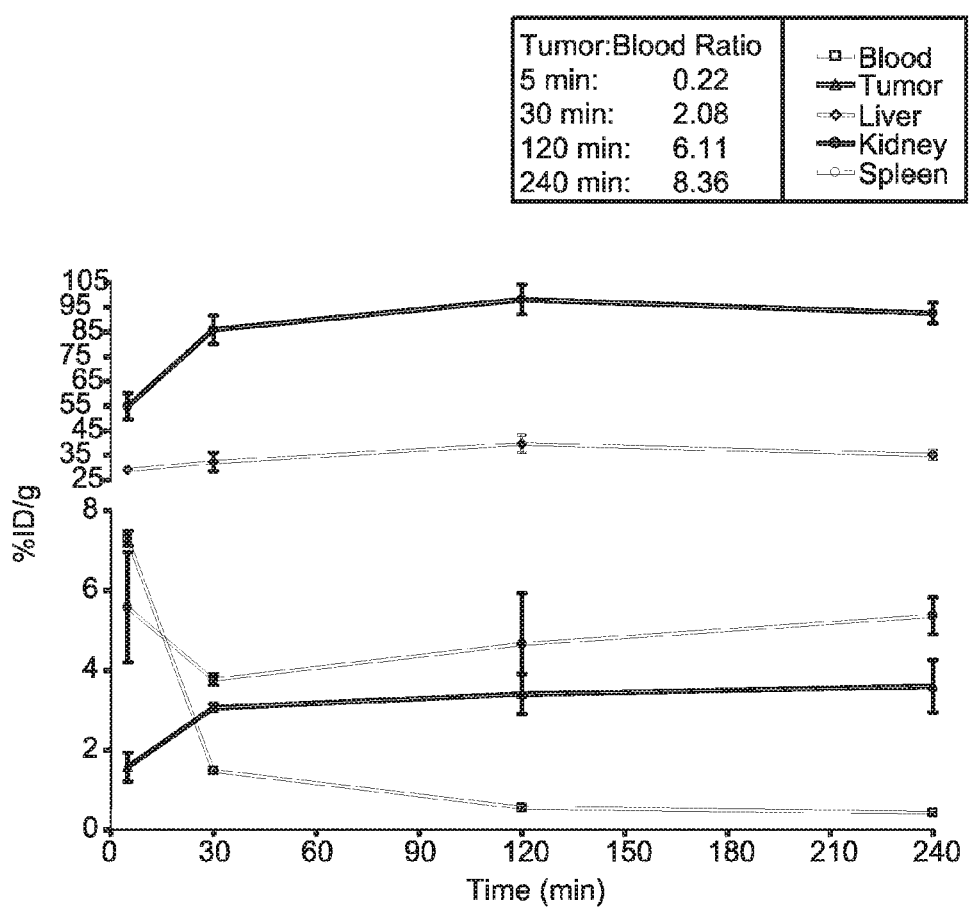
FIG. 6 is a graph of biodistribution profile of Z00477 (SEQ. ID No. 3) in blood, tumor, liver, kidney and spleen samples from SKOV3 tumor bearing mice, including the tumor:blood ratio over time.

The $^{99m}$Tc labeled Z00477 (SEQ. ID No. 4) polypeptide was injected into SKOV3 mice. FIG. 6 shows the tumor and blood curves for these experiments. The Z00477 (SEQ. ID No. 4) polypeptide shows good tumor uptake in target-expressing SKOV3 tumors, with a maximal value of approximately 3% of the injected dose per gram of tissue at 30 minutes post-injection (PI), and a peak tumor:blood ratio of more than 8 at 240 minutes PI.

Polypeptides exhibit a monoexponential clearance from the blood with half-lives of less than two minutes. This clearance is primarily mediated by the liver and kidneys. Polypeptide uptake in the spleen was moderate, and moderate to high uptake in the liver is observed, as described in Table 5.

Z00477 (SEQ. ID No. 3) dimer, (Z00477)$_2$ (SEQ. ID No. 5), was radiolabeled and used for a four-hour biodistribution experiment in SKOV3-tumored mice.

The monovalent and bivalent polypeptides otherwise exhibit similar biodistribution characteristics, and blood half-lives are observed for both in the one to two minute range. The results clearly indicate that both monomeric and divalent polypeptides can be targeted to HER2 in vivo.

Figure 7:
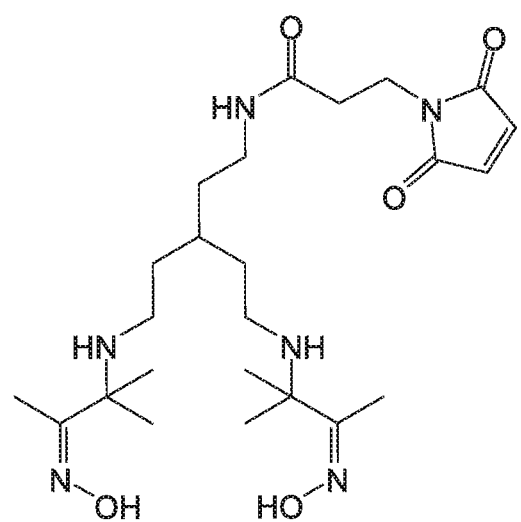
FIG. 7 is a diagram of the chemical structure for a Mal-cPN216 linker.

To introduce the $^{99m}$Tc chelator cPN216 (FIG. 7), a bifunctional compound Mal-cPN216 was synthesized comprising of a thiol-reactive maleimide group for conjugation to a terminal cysteine of a polypeptide and an amine oxime group for chelating $^{99m}$Tc.

cPN216-amine was obtained from GE Healthcare. N-ß-maleimidopropionic acid was purchased from Pierce Technologies (Rockford, Ill.). N-methylmorpholine, (benzotriazol-1-yloxy) tripyrrolidinophosphonium hexafluorophosphate (PyBoP), dithiothreitol (DTT), ammonium bicarbonate, and anhydrous DMF were purchased from Aldrich (Milwaukee, Wis.). PBS buffer (1×, pH 7.4) was obtained from Invitrogen (Carlsbad, Calif.). HPLC-grade acetonitrile (CH$_3$CN), HPLC-grade trifluoroacetic acid (TFA), and Millipore 18 m) water were used for HPLC purifications.

To an ice-cooled solution of N-ß-maleimidopropionic acid (108 mg, 0.64 mmol), cPN216-amine (200 mg, 0.58 mmol), and PyBoP (333 mg, 0.64 mmol) in anhydrous DMF at 0° C. was added 0.4 M of N-methylmorpholine in DMF (128 μL, 1.16 mmol). The ice bath was removed after 2 hrs, and the mixture was stirred at room temperature overnight before being subjected to HPLC purification. The product was obtained as a white powder (230 mg, 80% yield). 1H-NMR (400 MHz, DMSO-d6): δ 1.35 (m, 2H), 1.43 (s, 12H), 1.56 (m, 5H), 1.85 (s, 6H), 2.33 (dd, J1=8 Hz, J2=4 Hz, 2H), 2.78 (m, 4H), 3.04 (m, 2H), 3.61 (dd, J1=8 Hz, J2=4 Hz, 2H), 7.02 (s, 2H), 8.02 (s, 1H), 8.68 (s, 4H), 11.26 (s, 2H); m/z=495.2 for [M+H]$^+$ (C24H43N6O5, Calculated MW=495.3).

The polypeptide was dissolved with freshly degassed PBS buffer (1×, pH 7.4) at a concentration of approximately 1 mg/mL. The disulfide linkage in the polypeptide was reduced by the addition of DTT solution in freshly degassed PBS buffer (1×, pH 7.4). The final concentration of DTT was 20 mM. The reaction mixture was vortexed for 2 hours and

TABLE 5

| Z00477 (SEQ. ID No. 3) His6 (SEQ ID NO: 7)tagged uptake (% ID/g) in SKOV3 tumor bearing mice | | | | |
|---|---|---|---|---|
| | 5 Minutes | 30 Minutes | 120 Minutes | 240 Minutes |
| Blood | 7.30 ± 0.32 (n = 3) | 1.47 ± 0.16 (n = 3) | 0.56 ± 0.03 (n = 3) | 0.43 ± 0.03 (n = 3) |
| Tumor | 1.57 ± 0.62 (n = 3) | 3.06 ± 0.17 (n = 3) | 3.40 ± 0.87 (n = 3) | 3.60 ± 1.15 (n = 3) |
| Liver | 29.07 ± 0.70 (n = 3) | 32.19 ± 6.50 (n = 3) | 39.57 ± 6.29 (n = 3) | 35.17 ± 3.48 (n = 3) |
| Kidney | 54.83 ± 9.29 (n = 3) | 85.89 ± 10.00 (n = 3) | 97.99 ± 10.45 (n = 3) | 92.54 ± 7.36 (n = 3) |
| Spleen | 5.57 ± 2.39 (n = 3) | 3.76 ± 0.23 (n = 3) | 4.65 ± 2.21 (n = 3) | 5.36 ± 0.80 (n = 3) |

Figure 8A:
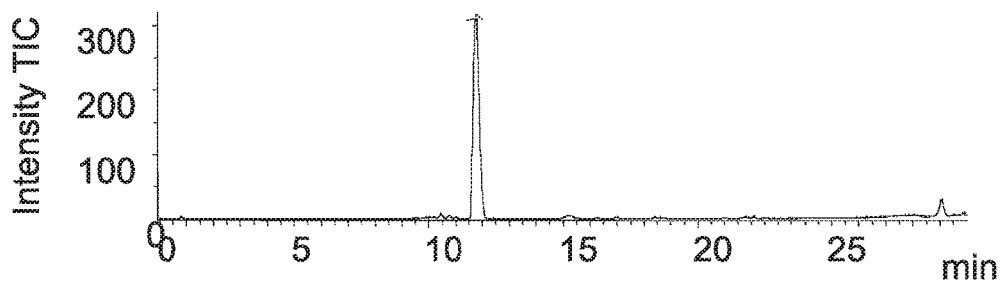
FIG. 8A is a graph of the electrospray ionization time of flight mass spectrum (ESI-TOF-MS) and FIG. 8B is a graph of mass deconvolution result for the purified Z00477 (SEQ. ID No. 3)-cPN216.
Figure 8B:
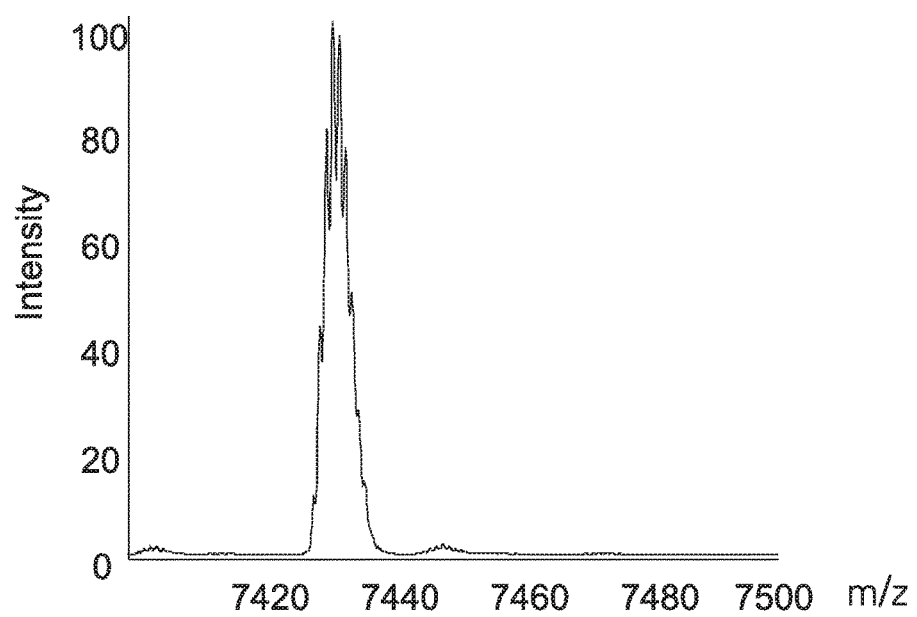

Bivalent polypeptides exhibit higher affinity than the corresponding monomers, presumably due to the avidity effect. Their larger size, however, may hinder tumor penetration. For the HER2 polypeptides, bivalent forms of each the four high affinity polypeptides were available. The passed through a Zeba desalt spin column (Pierce Technologies) pre-equilibrated with degassed PBS buffer (1×, pH 7.4) to remove excess of DTT reagent. The eluted reduced polypeptide molecule was collected, and the bifunctional compound Mal-cPN216 was added (20 equivalents per equivalent of the polypeptide) as a solution in DMSO, and the mixture was vortexed at room temperature for 3 hours and frozen with liquid-nitrogen. The reaction mixture was stored overnight before being subject to Reverse phase HPLC purification (FIGS. 8A and 8B).

The HPLC purification was performed on a MiCHROM Magic C18AQ 5 μ200 A column (MiChrom Bioresources, Auburn, Calif.). Solvent A: $H_2O$ (with 0.1% formic acid), Solvent B: $CH_3CN$ (with 0.1% formic acid). Gradient: 5-100% B over 30 mins.

The fractions containing desired product were combined and neutralized with 100 mM ammonium bicarbonate solution, and the solvents were removed by lyophilization to give the desired imaging agent composition as a white solid (yield 41%).

LC-MS analysis of the purified product confirmed the presence of the desired product, and the MW suggested that only one cPN216 label was added to polypeptide constructs (Z00477 (SEQ. ID No. 3)-cPN216: calculated MW: 7429 Da, found: 7429 Da; Z02891 (SEQ. ID No. 2)-cPN216 calculated MW: 7524 Da, found: 7524 Da).

To a 20 mL vial was added 10.00 mL of distilled, deionized water. Nitrogen gas was bubbled through this solution for approximately 30 minutes prior to addition of the $NaHCO_3$ (450 mg, $5.36 \times 10^{-3}$ mol), $Na_2CO_3$ (60 mg, $5.66 \times 10^{-4}$ mol) and sodium para-aminobenzoate (20 mg, $1.26 \times 10^{-4}$ mol). All reagents were weighed independently and added to the vial containing water. Tin chloride (1.6 mg, $7.09 \times 10^{-6}$ mol) and MDP (2.5 mg, $1.42 \times 10^{-5}$ mol) were weighed together into a 1 dram vial and subsequently transferred (with 1 subsequent wash) by rapid suspension in approximately 1 mL of the carbonate buffer mixture. 10 μL aliquots were removed and transferred under a stream of nitrogen to silanized vials, immediately frozen and maintained in a liquid nitrogen bath until lyophilization. Each vial was partially capped with rubber septa and placed in a tray lyophilizer overnight. Vials were sealed under vacuum, removed from the lyophilizer, crimp-sealed with aluminum caps, re-pressurized with anhydrous nitrogen and stored in a freezer until future use.

Synthesis of the radiolabeled polypeptide was performed using a one-step kit formulation produced in house (Chelakit A+) containing a lyophilized mixture of stannous chloride as a reducing agent for technetium, methylene diphosphonic acid, p-aminobenzoate as a free-radical scavenger and sodium bicarbonate/sodium carbonate (pH 9.2) as buffer. In rapid succession, 20 μL of a 2 μg/μL solution of polypeptide in saline was added to the Chelakit, followed immediately by $Na^{99m}TcO_4$ (0.8 mCi, 29.6 MBq) in 0.080 mL of saline (0.15M NaCl) obtained from Cardinal Health (Albany, N.Y.). The mixture was agitated once and allowed to sit at ambient temperature for 20 min. Upon completion, the crude radiochemical yield was determined by ITLC (Table 6 below according to ITLC-SG, Biodex, 0.9% NaCl).

TABLE 6

| Compound | Grade RCP (%) | purified RCP (%) | RCY (%) decaycorrected/ (uncorrected) |
|---|---|---|---|
| Z00477 (SEQ. ID No. 3) | 49.2 | 98.6 | 53.9 (13.1) |
| Z02891 (SEQ. ID No. 2) | 71.6 | 97.5 | 46.9 (43.8) |

Figure 9:
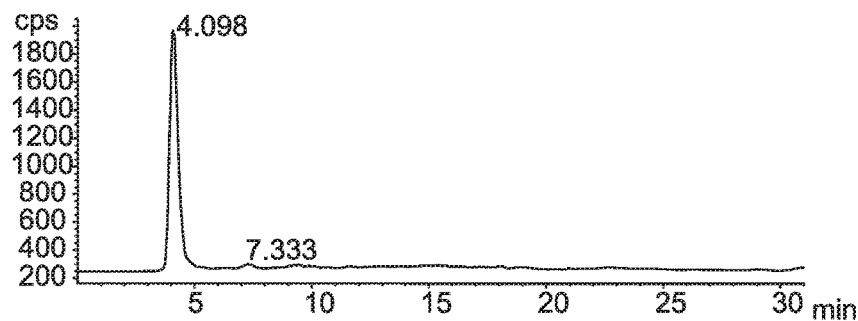
FIG. 9 is a reverse phase HPLC gamma trace chromatogram for Z02891-cPN216 (SEQ. ID No. 2) labeled with $^{99m}$Tc.

The reaction volume was increased to 0.45 mL with 0.35 mL of 150 mM sterile NaCl, and the final product purified by size exclusion chromatography (NAP5, GE Healthcare, charged with 10 mM PBS). The crude reaction mixture was loaded onto the NAP5 column, allowed to enter the gel bed and the final purified product isolated after elution with 0.8 mL of 10 mL PBS. Final activity was assayed in a standard dose calibrator (CRC-15R, Capintec, Ramsey, N.J.). Radiochemical yield (Table6) and purity were determined by ITLC (>98.5%), C4 RP-HPLC (FIG. 9) and SEC-HPLC analysis. The final product (10-15 μCi/μg, 0.2-0.5 μCi/μL (0.37 MBq/μg, 7.4 MBq/mL)) was used immediately for biodistribution studies.

The HPLC conditions used for this experiment were as follows: C4 RP-HPLC method 1: Solvent A: 95/5 $H_2O$/$CH_3CN$ (with 0.05% TFA), Solvent B: 95/5 $CH_3CN$/$ddH_2O$ (distilled, deionized water) with 0.05% TFA. Gradient elution: 0 min. 0% B, 4 min. 20% B, 16 min. 60% B, 20 min. 100% B, 25 min. 100% B, 26 min. 0% B, 31 min. 0% B.

C4 RP-HPLC method 2: Solvent A: 0.06% $NH_3$ in water, Solvent B: $CH_3CN$. Gradient elution: 0 min. 0% B, 4 min. 20% B, 16 min 60% B, 20 min. 100% B, 25 min 100% B, 26 min. 0% B, 31 min. 0% B.

RP-HPLC analysis performed on an HP Agilent 1100 with a G1311A QuatPump, G1313A autoinjector with 100 μL syringe and 2.0 mL seat capillary, Grace Vydac—protein C4 column (S/N E050929-2-1, 4.6 mm×150 mm), G1316A column heater, G1315A DAD and Ramon Star—GABI gamma-detector.

SEC HPLC: Solvent: 1× (10 mM) PBS (Gibco, Invitrogen, pH 7.4 containing $CaCl_2$ and $MgCl_2$). Isocratic elution for 30 min. Analysis performed on a: Perkin Elmer SEC-4 Solvent Environmental control, Series 410 LC pump, ISS 200 Advanced LC sample processor and Series 200 Diode Array Detector. A Raytest GABI with Socket 8103 0111 pinhole (0.7 mm inner diameter with 250 μL volume) flow cell gamma detector was interfaced through a Perkin Elmer NCI 900 Network Chromatography Interface. The column used was a Superdex 75 10/300 GL High Performance SEC column (GE Healthcare. code: 17-5174-01, ID no. 0639059).

Figure 5A:
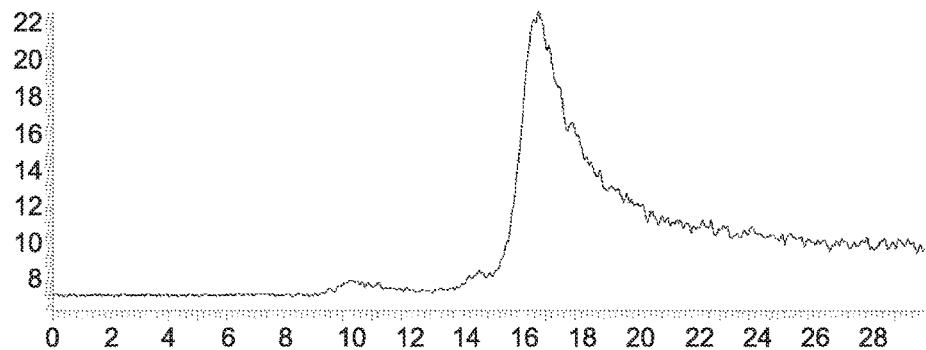
FIG. 5A is a size exclusion HPLC gamma chromatogram of aggregated $^{99m}$Tc(CO)$_3$(His6)Z00477 (SEQ. ID. No. 4) ('His6' disclosed as SEQ ID NO: 7) at pH 9.
Figure 5B:
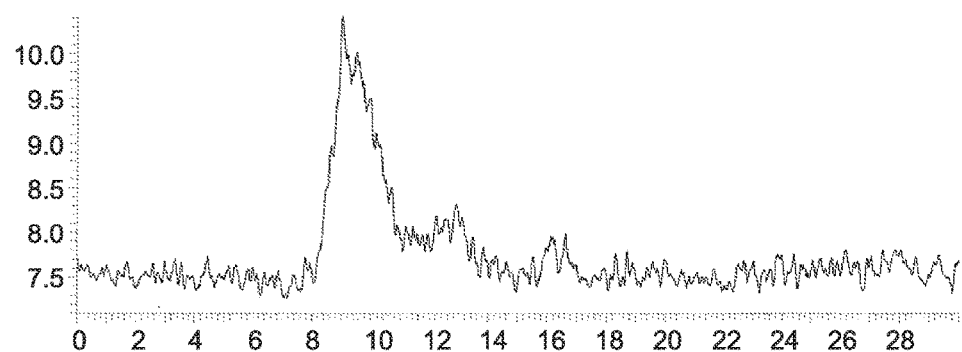
FIG. 5B a size exclusion HPLC gamma chromatogram of non aggregated $^{99m}$Tc(CO)$_3$(His6)Z00477 ('His6' disclosed as SEQ ID NO: 7) labeled affibody standard.

The operating pH of the Chelakits used to incorporate $^{99m}Tc$ into the cPN216 chelate (pH=9.2) nearly matched the calculated pI of the Z00477 (SEQ. ID No. 3) polypeptide. Labeling under these conditions were determined to cause aggregation in the final product (FIGS. 5A and 5B). Aggregation was confirmed by size exclusion HPLC and through the increased blood residence time and liver uptake observed in the biodistribution studies. By altering the isoelectric point of the polypeptide, $^{99m}Tc$ was successfully incorporated onto the Z02891 (SEQ. ID No. 2) construct. Size exclusion HPLC confirmed the presence of a species with the appropriate molecular weight and biodistribution studies showed uptake of the tracer into the tumor xenografts.

In vivo studies were carried out with female CD-1 nude mice (Charles River Labs, Hopkinton, Mass.) with an age range between 6 and 15 weeks. Mice were housed in a ventilated rack with food and water ad libitum and a standard 12 hours day-night lighting cycle. For xenografts, animals were injected with 100 μl of cells in PBS. Cells were implanted subcutaneously in the right hindquarter. Implantation was performed under isoflurane anesthesia. For SKOV3, between $3 \times 10^6$ to $4 \times 10^6$ cells were implanted in each mouse. Under these conditions, useable tumors (100 to 300 μg) were obtained in 3 to 4 weeks in greater than 80% of animals injected.

Mice were given tail-vein injections of ~1 ug of $^{99m}Tc$-labeled polypeptides (~10 μCi/1 μg). Mice were placed in filter-paper lined cages until euthanasia. Three mice were euthanized at each timepoint and tissues of interest dissected and counted on a Perkin Elmer Wallac Wizard 1480 Gamma Counter. Data were collected for blood, kidney, liver, spleen, and injection site (tail). Urine from cages was pooled with the bladder and also counted. The remaining tissues were counted and the sum of all tissues plus urine for each animal was summed to provide the total injected dose. The % injected dose for each organ was determined based on this total, and organs were weighed for determination of the % injected dose per gram, (% ID/g). Data is reported as mean value for all four to five mice in the time point with error bars representing the standard deviation of the group. Four time points were taken over four hours (5, 30, 120, and 240 minutes post-injection).

Figure 10:
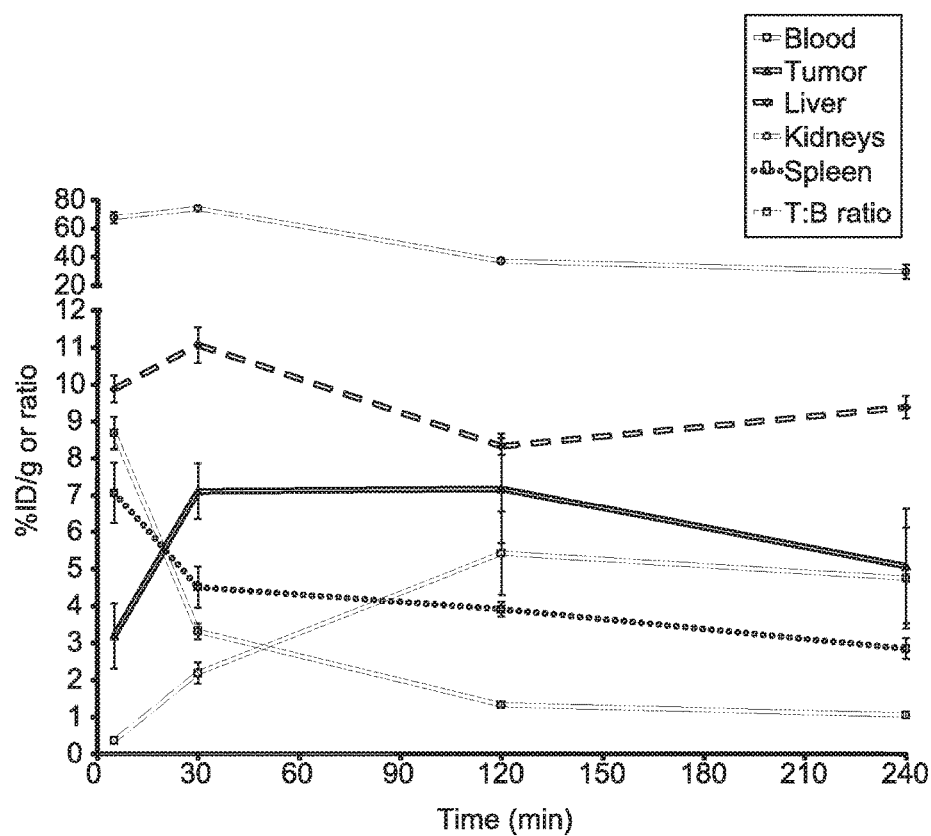
FIG. 10 is a graph of the biodistribution profile of Z02891 (SEQ. ID No. 2) labeled with $^{99m}$Tc via cPN216 (% ID, % injected sdose)) in blood, liver, kidneys, spleen, and tail samples from SKOV3 tumor bearing mice.
Figure 11:
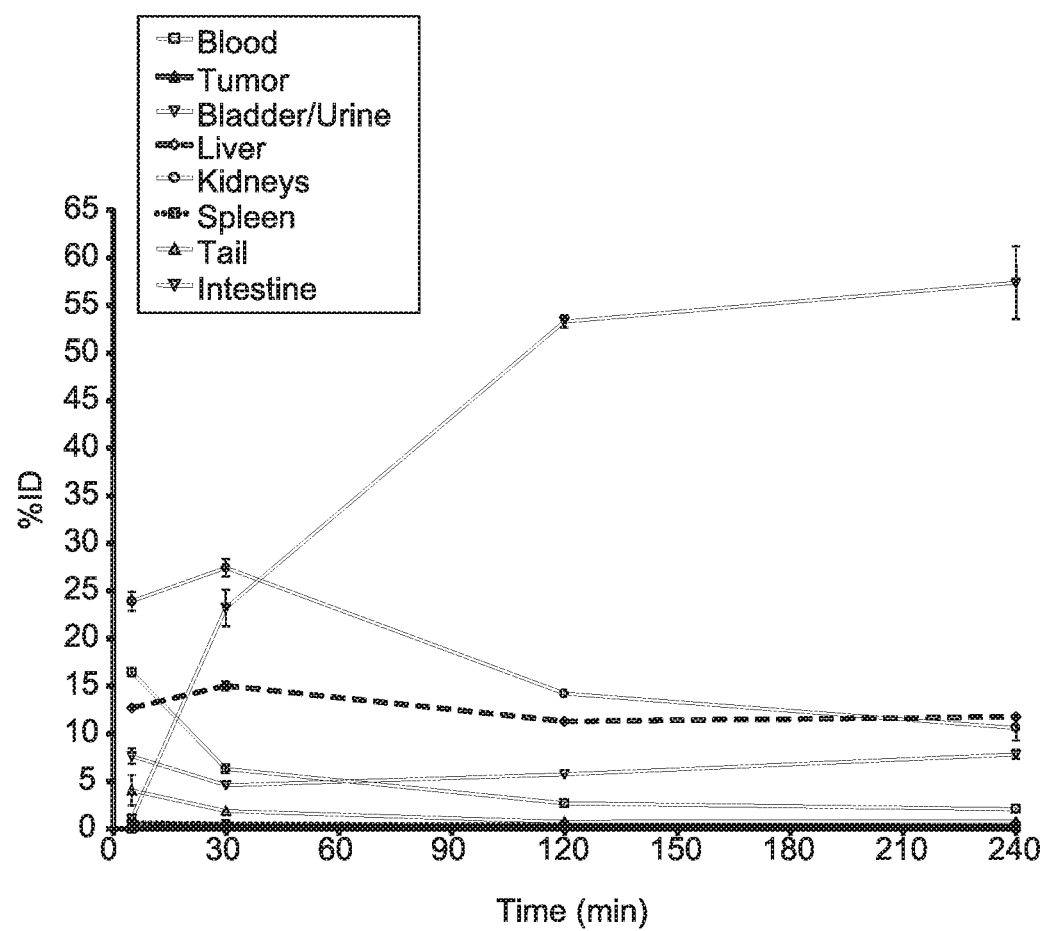
FIG. 11 is a graph of the biodistribution profile of Z02891 (SEQ. ID No. 2) labeled with $^{99m}$Tc via cPN216 (% ID, % injected dose) in tumor, blood, liver, kidneys, bladder/urine, tail, intestine and spleen samples from SKOV3 tumor bearing mice.
Figure 12:
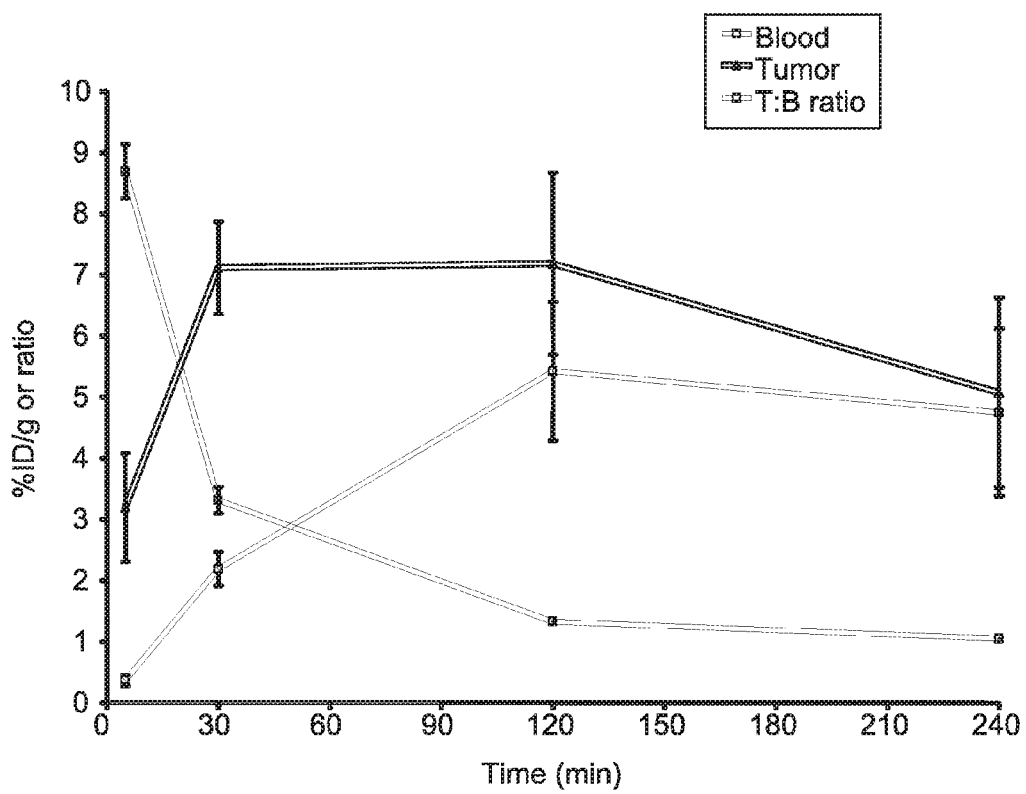
FIG. 12 is a graph of the biodistribution profile for Z02891 (SEQ. ID No. 2) in SKOV3 tumor bearing mice showing the tumor:blood ratio.

The Z02891 (SEQ. ID No. 2)-cPN216-$^{99m}$Tc polypeptide shows strong tumor uptake in target-expressing SKOV3 tumors, with a value of 7.11±1.69% (n=5) of the injected dose per gram of tissue at 30 minutes post-injection (PI), which remains fairly constant over the time-course of the study up to 240 min PI. Tumor:blood ratios were 2, 5, and 5 at 30, 120, and 240 min post injection, respectively. FIGS. 10, 11 and 12 show the tumor, blood and tumor:blood curves for these experiments.

The Polypeptides exhibit a monoexponential clearance from the blood with half-lives of less than two minutes. This clearance is primarily mediated by the kidneys, with 10.58±2.96 (n=5) ID/organ at 240 min post-injection PI. Activity is secreted primarily in the urine. Polypeptide uptake in the spleen was moderate to high due to possible aggregation, and moderate uptake in the liver is observed, e.g., 12% ID/organ (equivalent in value in mice to % ID/g) over the course of the study.

Biodistribution Results for Z02891 (SEQ. ID No. 2)-cPN216-$^{99m}$Tc

Dichloromethane, 2-(tert-butoxycarbonylaminooxy) acetic acid, triethylamine, N-(2-aminoethyl)maleimide trifluoroacetic acid (TFA) salt, N-hydroxybenzotriazole hydrate (HOBT), 1-ethyl-3-[3-dimethylaminopropyl]carbodiimide (EDC), dithiothriotol (DTT), and all other standard synthesis reagents were purchased from Sigma-Aldrich Chemical Co. (St. Louis, Mo.). All chemicals were used without further purification. PBS buffer (1×, pH 7.4) was obtained from Invitrogen (Carlsbad, Calif.). HPLC-grade ethyl acetate, hexanes, acetonitrile ($CH_3CN$), trifluoroacetic acid (TFA), and Millipore 18 mΩ water were used for purifications.

To a solution of 2-(tert-butoxycarbonylaminooxy)acetic acid (382 mg, 2 mmol) in anhydrous dichloromethane (20 mL) was added sequentially triethylamine (307 jut, 2.2 mmol), N-(2-aminoethyl)maleimide-TFA salt (508 mg, 2 mmol), HOBT (306 mg, 2 mmol), and EDC (420 mg, 2.2 mmol). After being stirred for 24 hrs at room temperature, the reaction mixture was diluted with ethyl acetate (50 mL) and washed with saturated sodium bicarbonate solution (3×30 mL), water (30 mL), and brine (30 mL) The organic layer was dried over anhydrous magnesium sulfate and filtered. The filtrate was concentrated to a pale yellow solid, which was purified by column chromatography (70% ethyl acetate in hexanes) to give the product as a white powder (500 mg, 80% yield). $^1$H-NMR (400 MHz, $CDCl_3$): δ 1.50 (s, 9H), 3.55 (tt, J1=6.0 Hz, J2=6.5 Hz, 2H), 3.77 (dd, J=7.6 Hz, 2H), 4.30 (s, 2H), 6.3 (s, 2H).

A solution of 9.3 mg of Mal-AO-Boc in 1 mL of 3M HCl in methanol was stirred at room temperature for 18 hours. Solvents were removed under vacuum to yield Mal-AO as a light yellow solid. (80% yield). $^1$H-NMR (400 MHz, DMSO-$d_6$): δ 3.27 $CH_2$ (t, J=4.0 Hz, 2H), 3.49 $CH_2$ (t, J=4.0

TABLE 7

Z02891 (SEQ. ID No. 2) cPN216 uptake (% ID/g) in SKOV3 tumor bearing mice

|  | 5 Minutes | 30 Minutes | 120 Minutes | 240 Minutes |
| --- | --- | --- | --- | --- |
| Blood | 8.69 ± 0.99 (n = 5) | 3.32 ± 0.48 (n = 5) | 1.33 ± 0.05 (n = 5) | 1.05 ± 0.09 (n = 5) |
| Tumor | 3.19 ± 1.78 (n = 4) | 7.11 ± 1.69 (n = 5) | 7.18 ± 3.33 (n = 5) | 5.07 ± 3.47 (n = 5) |
| Liver | 9.87 ± 0.81 (n = 5) | 11.07 ± 1.06 (n = 5) | 8.33 ± 0.50 (n = 5) | 9.38 ± 0.69 (n = 5) |
| Kidney | 67.61 ± 9.24 (n = 5) | 74.15 ± 4.17 (n = 5) | 37.14 ± 3.48 (n = 5) | 29.67 ± 10.87 (n = 5) |
| Spleen | 7.07 ± 1.84 (n = 5) | 4.51 ± 1.25 (n = 5) | 3.91 ± 0.44 (n = 5) | 2.85 ± 0.62 (n = 5) |

Z00477 (SEQ. ID. NO. 4), Z00342 (SEQ. ID No. 1) and Z02891 (SEQ. ID No. 2)-cysteine polypeptides were functionalized with an aminoxy group via an engineered C-terminal cysteine. The purity of the polypeptide molecules provided was determined to be >95% by High Performance Liquid Chromatography (HPLC).

Figure 13A:
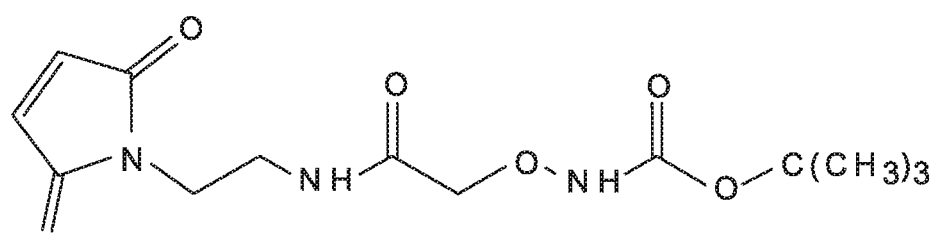
FIGS. 13A and 13B are diagrams of the chemical structures for Boc-protected malimide-aminoxy (Mal-AO-Boc) and malimide-aminoxy (Mal-AO) linkers. 13A is the chemical structure for tert-butyl 2-(2-(2,5-dioxo-2,5-dihydro-1H-pyrrol-1-yl)ethylamino)-2-oxoethoxycarbamate (Mal-AO-Boc) and 13B is the chemical structure for 2-(aminooxy)-N-(2-(2,5-dioxo-2,5-dihydro-1H-pyrrol-1-yl)ethyl) acetamide hydrochloride (Mal-AO.HCl).
Figure 13B:
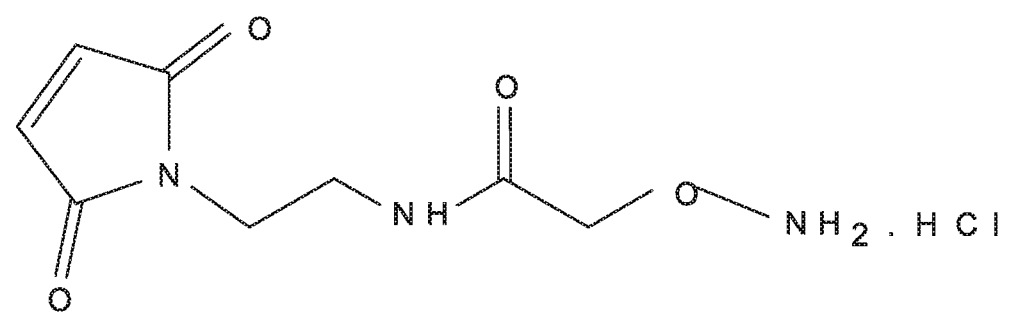

To incorporate $^{18}$F into the Polypeptide molecules, a bifunctional linker Mal-AO was synthesized comprising of two orthogonal groups: a thiol-reactive maleimide group for conjugation to the engineered cysteine and an aldehyde-reactive aminoxy group (FIGS. 13A and 13B). This linker was prepared by reacting N-(2-aminoethyl) malemide with 2-(tert-butoxycarbonylaminooxy) acetic acid using 1-ethyl-3-[3-dimethylaminopropyl] carbodiimide (EDC)-mediated coupling conditions yielding the Boc-protected form of the linker. The Boc protecting group was then de-protected by acid cleavage to give the final Mal-AO product in quantitative yield. The final product was used directly without further purification.

Hz, 2H), 4.39 $CH_2O$ (s, 2H), 7.00 CH═CH (s, 2H); m/z=214.07 for [M+H]$^+$ ($C_8H_{12}N_3O_4$, Calculated MW=214.11))

The polypeptide was dissolved with freshly degassed PBS buffer (1×, pH 7.4) at a concentration of approximately 1 mg/mL The disulfide linkage in the polypeptide was reduced by the addition of dithiothreitol (DTT) solution in freshly degassed PBS buffer (1×, pH 7.4). The final concentration of DTT is 20 mM. The reaction mixture was vortexed for 2 hours and eluted through a Zeba desalt spin column (Pierce Technologies) pre-equilibrated with degassed PBS buffer to remove excess of DTT reagent. The reduced polypeptide was collected, and the bifunctional Mal-AO compound was added (15 equivalents per equivalent of the polypeptide) as a solution in DMSO. After being vortexed at room temperature overnight, the reaction mixture was purified with High Performance Liquid Chromatography (HPLC) (FIGS. 14A and 14B).

The HPLC purification was performed on a MiCHROM Magic C18AQ 5µ 200 A column (MiChrom Bioresources, Auburn, Calif.). Solvent A: $H_2O$ (with 0.1% formic acid), Solvent B: $CH_3CN$ (with 0.1% formic acid). Gradient: 5-100% B over 30 mins. The fractions containing desired product was combined and neutralized with 100 mM ammonium bicarbonate solution, and the solvents were removed by lyophilization to give the aminoxy-modified polypeptide as a white solid.

ESI-TOF-MS analysis confirmed the presence of target product with the expected molecular weights (calculated MW: 6964 Da, 8531 Da, and 7243 Da, found: 6963 Da, 8532 Da, and 7244 Da for Z00477 (SEQ. ID No. 4)-$ONH_2$, Z00342 (SEQ. ID No. 1)-$ONH_2$, and Z02891 (SEQ. ID No. 2)-$ONH_2$, respectively.

Methods: All reactions were performed either under a nitrogen atmosphere or in a crimp-top sealed vial purged with nitrogen prior to use. Kryptofix 222 (Aldrich) and $K_2CO_3$ (EMD Science) were purchased and used as received. Optima™-grade acetonitrile was used as both HPLC and reaction solvents.

$K^{18}F$ (40 mCi·$mL^{-1}$ (1480 MBq·$mL^{-1}$) in purified water) was obtained from IBA Molecular (Albany, N.Y.) and PET-NET Solutions (Albany, N.Y.) and were used as received. The [$^{18}F^-$] fluoride was first immobilized on a Chromafix 30-PS-HCO3 anion exchange cartridge (ABX, Radeberg, Germany), then eluted into a drydown vessel with a 1 mL, 4:1 mixture of acetonitrile: distilled, deionized $H_2O$ ($ddH_2O$) containing Kryptofix K222 (376 g·$mol^{-1}$, 8 mg, $2.13 \times 10^{-5}$ mol) and potassium carbonate (138.2 g·$mol^{-1}$, 2.1 mg, $1.52 \times 10^{-5}$ mol). The solvent was removed under partial vacuum and a flow of nitrogen with gentle heating (~45° C.) (~15 min). The source vial and anion exchange cartridge were then washed with 0.5 mL of acetonitrile containing K222 (8 mg) and the reaction mixture again brought to dryness under partial vacuum and gentle heating (~10 min). The reaction vessel was repressurized with nitrogen and the azeotropic drydown repeated once with an additional 0.5 mL of acetonitrile. 4-formyl-N,N,N-trimethylanilinium triflate (313.30 g·$mol^{-1}$, 3.1 mg, $9.89 \times 10^{-6}$ mol) was dissolved in 0.35 mL of anhydrous DMSO (Acros) and added directly to the reaction vessel containing the OF K222, $K_2CO_3$. The reaction mixture was heated to 90° C. for 15 min and immediately cooled and quenched with 3 mL of $ddH_2O$. This mixture was subsequently passed through a cation exchange cartridge (Waters SepPak Light Accell Plus CM), diluted to 10 mL with $ddH_2O$, and loaded onto a reverse phase C18 SepPak (Waters SepPak Plus C18). The SepPak was flushed with 10 mL of $ddH_2O$ then purged with 30 mL of air. [$^{18}F$]4-fluorobenzaldehyde ($^{18}FBA$), was eluted in 1.0 mL of methanol.

Figure 15:
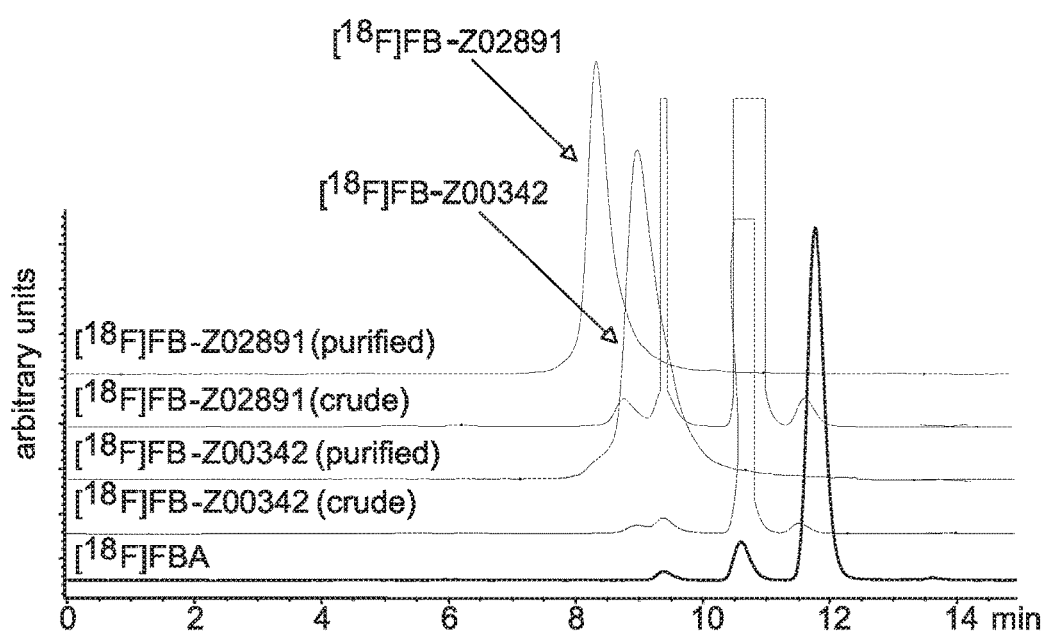
FIG. 15 is the reverse phase HPLC gamma chromatogram for the crude reaction mixtures and purified final products of $^{18}$F-fluorobenzyl-Z00342 (SEQ. ID No. 1) and $^{18}$F-fluorobenzyl-Z02891' (SEQ. ID No. 2).

Separately, a high recovery vial (2 mL, National Scientific) was charged with either the Z00477-(SEQ. ID No. 3)-$ONH_2$ (0.35-0.5 mg), Z00342-(SEQ. ID No.1)-$ONH_2$ (0.35-0.5 mg) or Z02891-(SEQ. ID No. 2)-$ONH_2$ (0.35-0.5 mg). The solid was suspended in 25 µL of $ddH_2O$ and 8 µL of trifluoroacetic acid. 25 µL of $^{18}FBA$ in methanol (see above) was transferred to the reaction vial. The vessel was capped, crimped, placed in a heating block and maintained at 60° C. for 15 minutes; at which point a small aliquot (<5 µt) was removed for analytical HPLC analysis. 450 µL of $ddH_2O$ with 0.1% TFA was used to dilute the solution to approx. 500 µL in preparation for semi-preparative HPLC purification. $^{18}FB$-Polypeptide was isolated and purified by semi-preparative HPLC. The HPLC fraction containing the product (0.113 mCi/4.18 MBq) was diluted 5:1 with $ddH_2O$ and subsequently immobilized on a tC18 Plus Sep Pak (Waters). The SepPak was flushed first with 5 mL of $ddH_2O$ then 30 mL of air. $^{18}FB$-Polypeptide was isolated in a minimal amount of ethanol by first eluting the void volume (approx. 0.5 mL) followed by collecting 250 to 300 µL of eluent in a separate flask. RP-HPLC analysis was performed on the isolated product in order to establish radiochemical and chemical purity. Typically, 10 µL of a 0.1 µCi/µL solution was injected for post formulation analysis. Isolated radiochemical yields are indicated in Table 9 and are decay corrected from the addition of polypeptide to $^{18}FBA$ and radiochemical purity of >99%. Alternatively, $^{18}F$-labeled polypeptides were isolated by NAP5 size exclusion chromatography by diluting the reaction mixture to approximately 0.5 mL with 10 mM PBS and loading onto the gel. The $^{18}F$-labeled polypeptides were isolated by eluting the column with 0.8 mL of 10 mM PBS and used without further modification. These results are illustrated in Table 8, and FIG. 15.

TABLE 8

| Compound | Yield isolated (decay corrected) (%) | HPLC RCP (%) |
| --- | --- | --- |
| Z00477 (SEQ. ID No. 4) | 0.6%/1.2% | 95% |
| Z00342 (SEQ. ID No. 1) | 8.2% (10.7%) | >99% |
| Z02891 (SEQ. ID No. 2) | 6.2% (7.6%) | >99% |

Analytical HPLC conditions used are as follows: Analysis performed on an HP Agilent 1100 with a G1311A QuatPump, G1313A autoinjector with 100 µL syringe and 2.0 mL seat capillary, Phenomenex Gemini C18 column (4.6 mm×150 mm), 5µ, 100 Å (S/N 420477-10), G1316A column heater, G1315A DAD and Ramon Star—GABI gamma-detector. 95:5 $ddH_2O$:$CH_3CN$ with 0.05% TFA, Solvent B: $CH_3CN$ with 0.05% TFA. Gradient elution (1.0 mL $min^{-1}$): 0 min. 0% B, 1 min. 15% B, 21 min. 50% B, 22 min. 100% B, 26 min. 100% B, 27 min. 0% B, 32 min. 0% B. or gradient elution (1.2 mL $min^{-1}$): 0 min 0% B, 1 min. 15% B, 10 min. 31% B, 10.5 min. 100% B, 13.5 min. 100% B, 14 min. 0% B, 17 min. 0% B.

Semipreparative HPLC conditions used are as follows: Purification was performed on a Jasco LC with a DG-2080-54 4-line Degasser, an MX-2080-32 Dynamic Mixer and two PU-2086 Plus Prep pumps, an AS-2055 Plus Intelligent autoinjector with large volume injection kit installed, a Phenomenex 5µ Luna C18(2) 100 Å, 250×10 mm, 5µ column with guard (S/N 295860-1, P/N 00G-4252-N0), an MD-2055 PDA and a Carroll & Ramsey Associates Model 1055 Analogue Ratemeter attached to a solid-state SiPIN photodiode gamma detector. Gradient elution: 0 min. 5% B, 32 min. 20% B, 43 min. 95% B, 46 min. 95% B, 49 min. 5% B, Solvent A: $ddH_2O$:$CH_3CN$ with 0.05% TFA, Solvent B: $CH_3CN$ with 0.05% TFA.

In vivo studies were carried out with female CD-1 nude mice (Charles River Labs, Hopkinton, Mass.) with an age range between 6 and 15 weeks. Mice were housed in a ventilated rack with food and water ad libitum and a standard 12 hour day-night lighting cycle. For xenografts, animals were injected with 100 μl of cells in PBS. Cells were implanted subcutaneously in the right hindquarter. Implantation was performed under isoflurane anesthesia. For SKOV3, between 3×10$^6$ to 4×10$^6$ cells were implanted in each mouse. Under these conditions, useable tumors (100 to 300 μg) were obtained in 3 to 4 weeks in greater than 80% of animals injected.

Mice were given tail-vein injections of ~1 ug of $^{18}$F-labeled polypeptide (~4 uCi/1 μg). Mice were placed in filter-paper lined cages until euthanasia. Three mice were euthanized at each timepoint and tissues of interest dissected and counted on a Perkin Elmer Wallac Wizard 1480 Gamma Counter. Data were collected for blood, kidney, liver, spleen, bone and injection site (tail). Urine from cages was pooled with the bladder and also counted. The remaining tissues were counted and the sum of all tissues plus urine for each animal was summed to provide the total injected dose. The percent injected dose for each organ was determined based on this total, and organs were weighed for determination of the percent injected dose per gram, (% ID/g). Data is reported as mean value for all three mice in the timepoint with error bars representing the standard deviation of the group.

Figure 16:
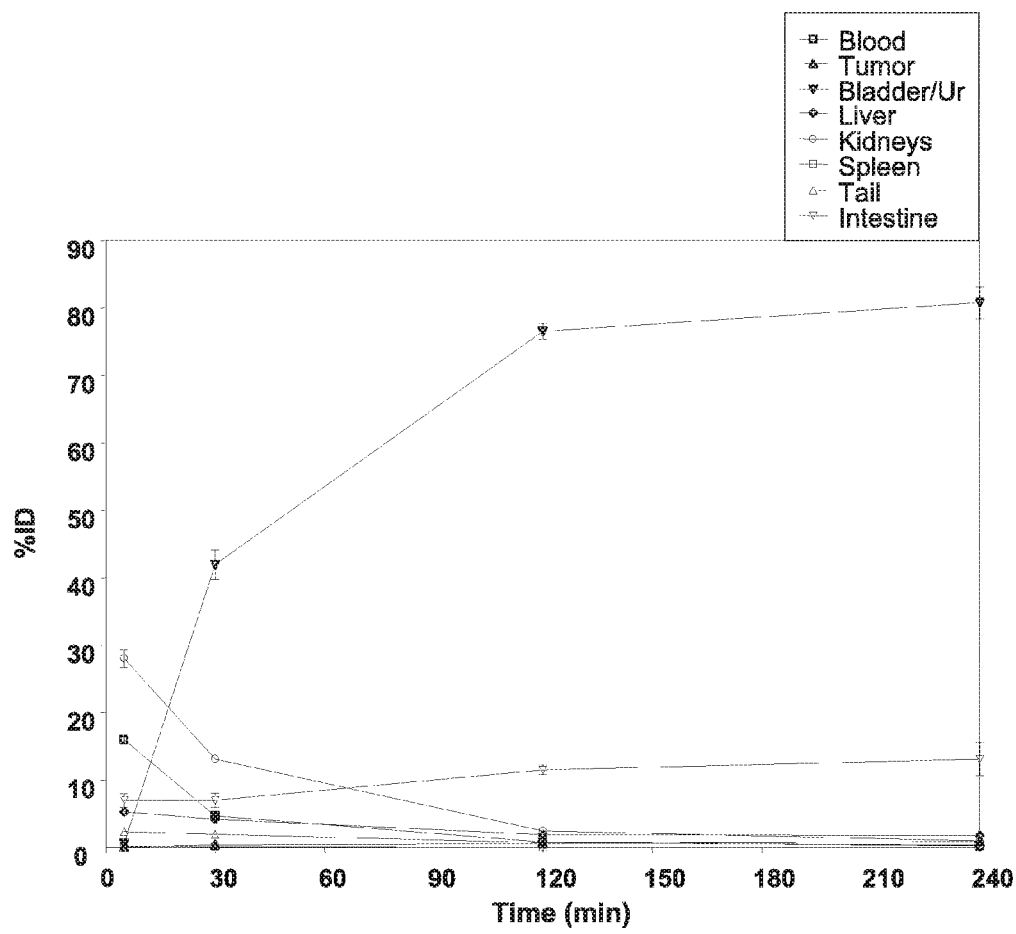
FIG. 16 is a graph of the biodistribution profile (% ID, % injected dose) of the Z02891 (SEQ. ID No. 2) polypeptide labeled with $^{18}$F from SKOV3-tumored animals.
Figure 17:
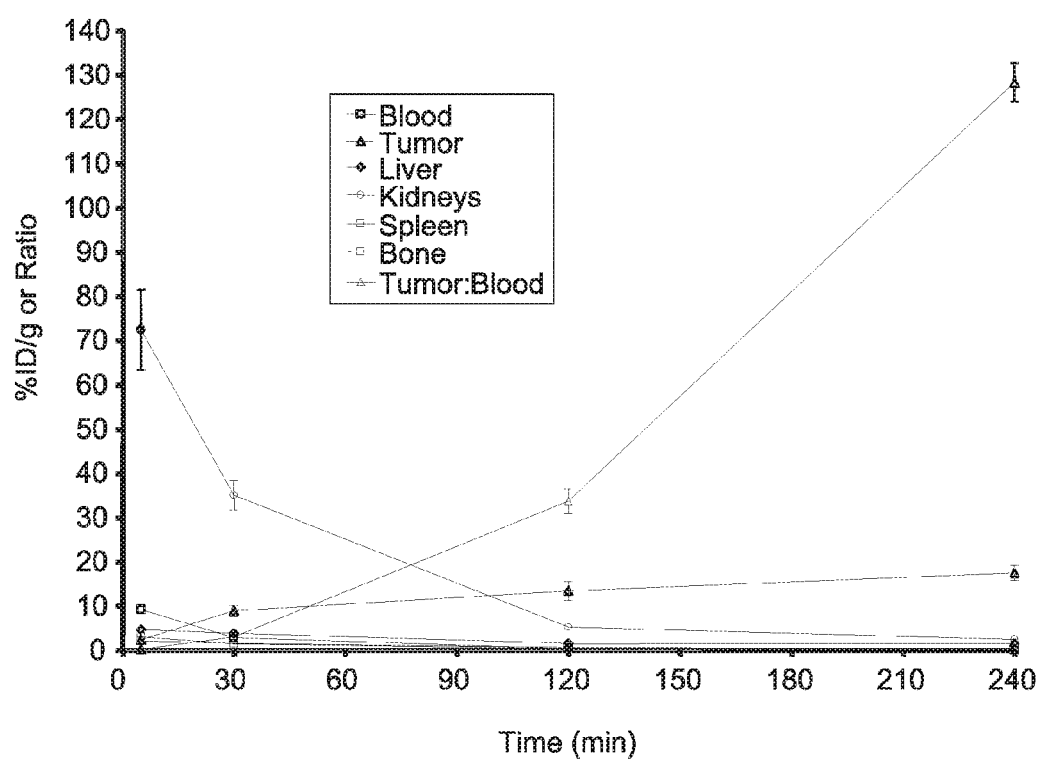
FIG. 17 is a graph of the biodistribution profile of Z02891 (SEQ. ID No. 2) polypeptide labeled with $^{18}$F (% ID, % injected dose) and the tumor:blood ratio from SKOV3-tumored animals.
Figure 18:
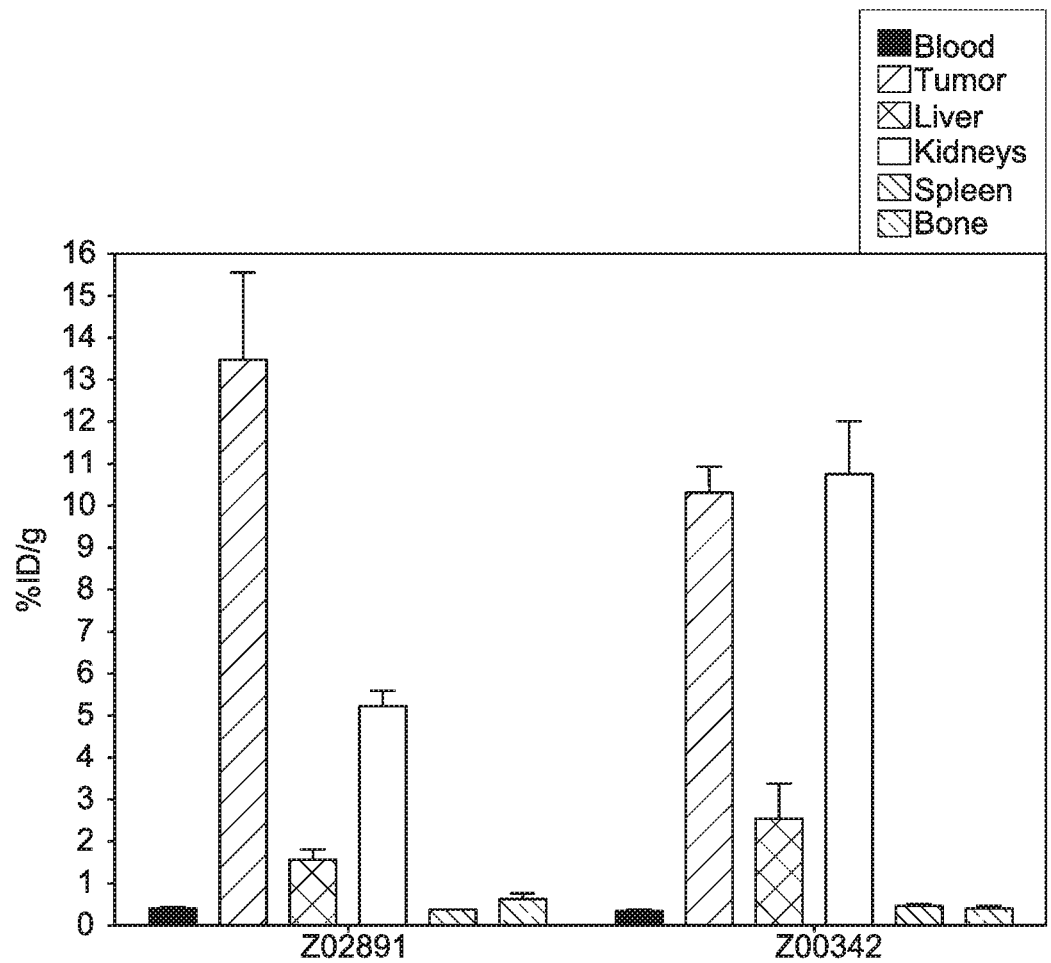
FIG. 18 is bar graph of the biodistribution profile (% ID, % injected dose) of $^{18}$F labeled Z00342 (SEQ. ID No. 1) and $^{18}$F labeled Z02891 (SEQ. ID No. 2) in blood, tumor, liver, kidneys, spleen and bone samples.

The polypeptides underwent biodistribution studies in SKOV3 cell xenograft models. Four time points were taken over four hours (5, 30, 120, and 240 minutes post-injection). Complete biodistribution data are included in table 12 (% ID/g Z02891 (SEQ. ID No. 2)-$^{18}$F-fluorobenzyl oxime in SKOV3 Tumor Bearing Mice) and table 13 (% ID/g Z00342 (SEQ. ID No. 1)$^{18}$F-fluorobenzyl oxime in SKOV3 Tumor Bearing Mice). FIGS. 16, 17 and 18 show the tumor, blood, tumor:blood, and clearance curves for these tests.

The Z02891 (SEQ. ID No. 2)$^{18}$F-fluorobenzyl oxime polypeptide shows strong tumor uptake in target-expressing SKOV3 tumors, with a value of 17.47±2.89 (n=3) of the injected dose per gram of tissue at 240 minutes post-injection (PI). Tumor:blood ratios were approximately 3, 34, and 128 at 30, 120, and 240 min post injection, respectively. The Z00342 (SEQ. ID No. 1)$^{18}$F-fluorobenzyl oxime polypeptide shows strong tumor uptake in target-expressing SKOV3 tumors, with a value of 12.45±2.52 (n=3) of the injected dose per gram of tissue at 240 minutes PI. Tumor:blood ratios were approximately 3, 32 and 53 at 30, 120 and 240 min post injection, respectively.

The polypeptides exhibit a monoexponential clearance from the blood with half-lives of less than two minutes. This clearance of Z02891 (SEQ. ID No. 2) is primarily mediated by the kidneys, with 0.95±0.07 (n=3) ID/organ at 240 min PI. Activity is secreted primarily in the urine. Polypeptide uptake in the spleen was minimal, and low uptake in the liver is observed, ca. 1.8% ID/organ (equivalent in value in mice to % ID/g) over the course of the study (four hours post injection).

TABLE 9

Z02891 (SEQ. ID No. 2) $^{18}$F-fluorobenzyl oxime uptake (% ID/g) in SKOV-3 tumor bearing mice

|  | 5 Minutes | 30 Minutes | 120 Minutes | 240 Minutes |
| --- | --- | --- | --- | --- |
| Blood | 9.23 ± 0.68 (n = 3) | 2.91 ± 0.23 (n = 3) | 0.40 ± 0.07 (n = 3) | 0.14 ± 0.02 (n = 3) |
| Tumor | 2.39 ± 1.13 (n = 3) | 8.91 ± 2.09 (n = 3) | 13.47 ± 3.61 (n = 3) | 17.47 ± 2.89 (n = 3) |
| Liver | 4.68 ± 0.45 (n = 3) | 3.85 ± 0.95 (n = 3) | 1.57 ± 0.42 (n = 3) | 1.59 ± 0.83 (n = 3) |
| Kidney | 72.42 ± 15.61 (n = 3) | 35.02 ± 5.76 (n = 3) | 5.22 ± 0.65 (n = 3) | 2.49 ± 0.17 (n = 3) |
| Spleen | 3.04 ± 1.15 (n = 3) | 1.46 ± 0.05 (n = 3) | 0.37 ± 0.01 (n = 3) | 0.26 ± 0.04 (n = 3) |

TABLE 10

Z00342 (SEQ. ID No. 1) $^{18}$F-fluorobenzyl oxime uptake (% ID/g) in SKOV-3 tumor bearing mice

|  | 5 Minutes | 30 Minutes | 120 Minutes | 240 Minutes |
| --- | --- | --- | --- | --- |
| Blood | 7.38 ± 0.72 (n = 3) | 1.76 ± 0.09 (n = 3) | 0.33 ± 0.08 (n = 3) | 0.87 ± 0.98 (n = 3) |
| Tumor | 2.54 ± 0.00 (n = 2) | 4.97 ± 3.14 (n = 3) | 10.30 ± 1.08 (n = 3) | 12.45 ± 2.52 (n = 3) |
| Liver | 8.29 ± 0.41 (n = 3) | 6.94 ± 0.92 (n = 3) | 2.54 ± 1.44 (n = 3) | 1.41 ± 0.35 (n = 3) |
| Kidney | 78.93 ± 2.93 (n = 3) | 30.94 ± 4.93 (n = 3) | 10.75 ± 2.17 (n = 3) | 4.91 ± 0.63 (n = 3) |
| Spleen | 3.85 ± 0.51 (n = 3) | 1.77 ± 0.34 (n = 3) | 0.47 ± 0.08 (n = 3) | 0.23 ± 0.05 (n = 3) |

All reactions are performed either under a nitrogen atmosphere or in a crimp-top sealed vial purged with nitrogen. Optima™-grade acetonitrile is used as both HPLC and reaction solvents.

[$^{123}$I]4-iodobenzaldehyde ($^{123}$I BA) is added to a high recovery vial (2 mL, National Scientific) containing the polypeptide-ONH$_2$ (Z02891, SEQ. ID No. 2), 0.35-0.5 mg). The reaction commences by dissolving the polypeptide in 25 μL of ddH$_2$O and adding 8 μL of trifluoroacetic acid followed by the addition of $^{123}$IBA in methanol. The vessel is capped, crimped, placed in a heating block and maintained at 60° C. for 15 minutes; removing a small aliquot (<5 μL) for analytical HPLC analysis is done to assess the status of the reaction. The reaction mixture is diluted to a minimum 1:1 mixture of ddH$_2$O: Acetonitrile mixture containing 0.1% TFA in preparation for semi-preparative HPLC purification. $^{123}$IB-Polypeptide is isolated and purified by semi-preparative HPLC or NAP5 size exclusion chromatography. The HPLC fraction containing the product is further diluted (5:1) with ddH$_2$O and subsequently immobilized on a tC18 Plus Sep Pak (Waters). Flushing the SepPak first with 5 mL of ddH$_2$O then 30 mL of air gives the $^{123}$IB-Polypeptide in a minimal amount of ethanol by first eluting the void volume (approx. 0.5 mL) followed by collecting 250 to 300 μL of eluent in a separate flask. RP-HPLC analysis is performed on the isolated product to establish radiochemical and chemical purity.

Figure 19:
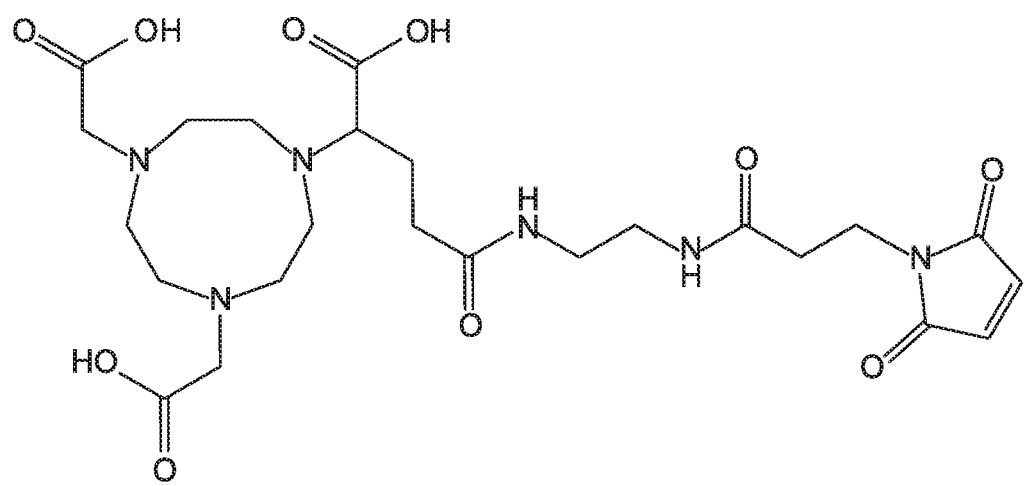
FIG. 19 is a diagram of the chemical structure of the Mal-NOTA linker.

Polypeptide Z00477 (SEQ. ID 3) was labeled with Ga, specifically $^{67}$Ga, after a NOTA (1,4,7-triazacyclononane-N,N',N"-triacetic acid) chelator was conjugated to the polypeptide. (FIG. 19)

Bioconjugation of Mal-NOTA to polypeptide molecules was accomplished as follows. The polypeptide was dissolved with freshly degassed PBS buffer (1×, pH 7.4) at a concentration of approximately 1 mg/mL. The disulfide linkage in the polypeptide was reduced by the addition of DTT solution in freshly degassed PBS buffer (1×, pH 7.4). The final concentration of DTT was 20 mM. The reaction mixture was vortexed for 2 hours and passed through a Zeba desalt spin column (Pierce Technologies) pre-equilibrated with degassed PBS buffer (1×, pH 7.4) to remove excess of DTT reagent. The eluted reduced polypeptide molecule was collected, and the bifunctional compound mal-NOTA was added (15 equivalents per equivalent of the polypeptide) as a solution in DMSO, and the mixture was vortexed at room temperature. The reaction was allowed to proceed overnight to ensure the complete conversion of the polypeptide molecules.

Figure 20A:
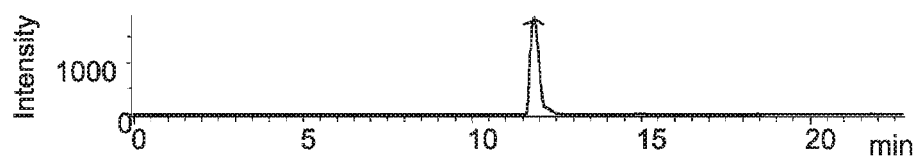
FIG. 20A is a graph of the electrospray ionization time of flight mass spectrum (ESI-TOF-MS), and 20B is a graph of the ESI-TOF-MS mass deconvolution result for Z00477 (SEQ. ID No. 3)-NOTA.

The HPLC purification was performed on a MiCHROM Magic C18AQ 5μ 200 A column (MiChrom Bioresources, Auburn, Calif.). Solvent A: H$_2$O (with 0.1% formic acid), Solvent B: CH$_3$CN (with 0.1% formic acid). Gradient: 5-100% B over 30 mins. (FIG. 20A)

The fractions containing desired product were combined and neutralized with 100 mM ammonium bicarbonate solution, and the solvents were removed by lyophilization to give the conjugated polypeptide as a white solid.

Figure 20B:
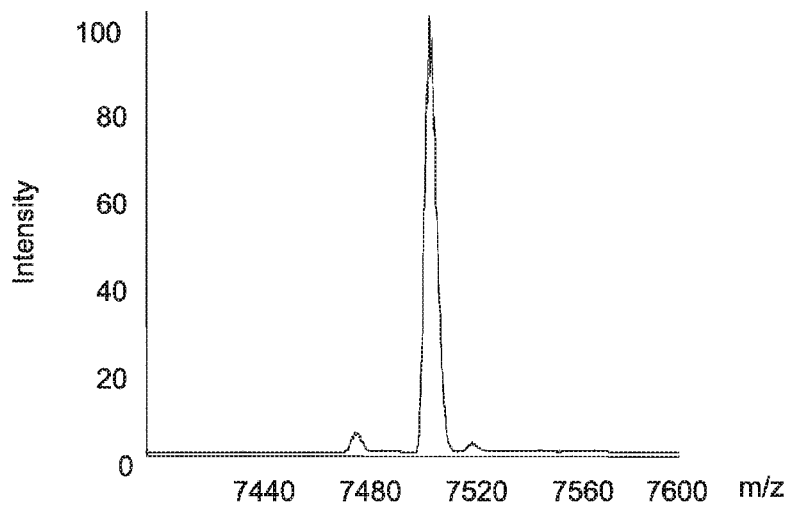

LC-MS analysis of the purified product confirmed the presence of the desired product, and the MW suggested that only one NOTA chelator was added to the polypeptide construct (calculated MW: 7504 Da, found: 7506 Da for Z00477 (SEQ. ID No. 3)-NOTA). (FIG. 20B)

Figure 21:
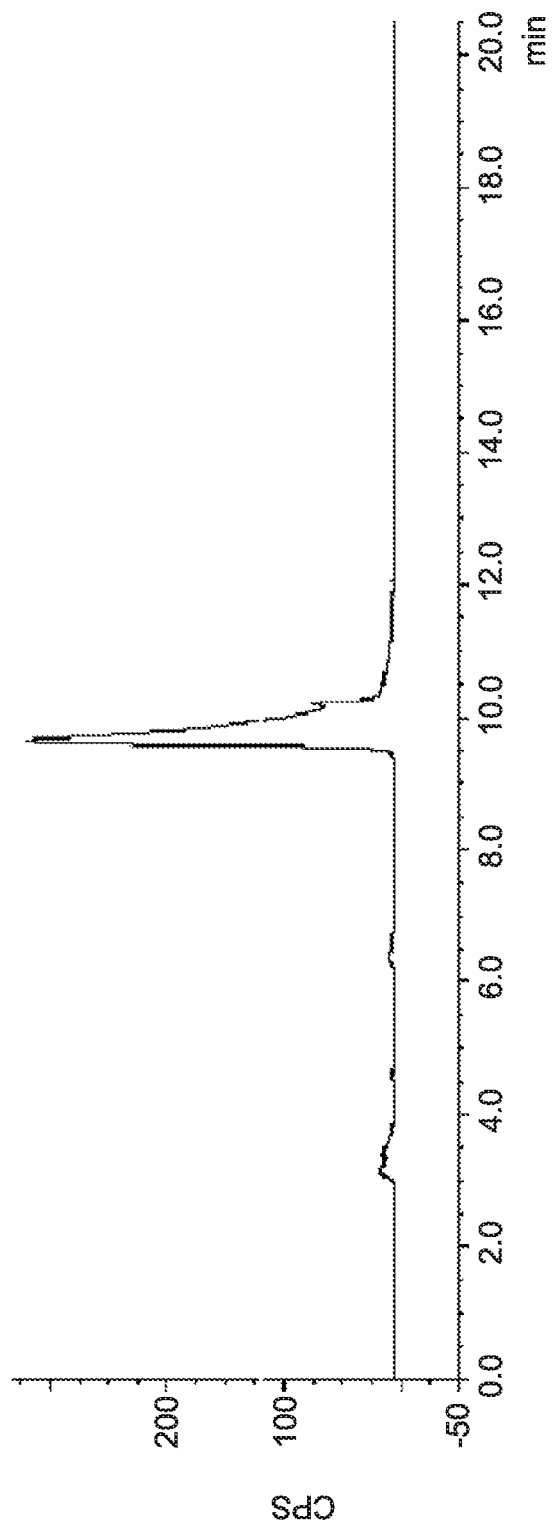
FIG. 21 is a graph of the reverse phase HPLC gamma trace for the crude reaction mixture of $^{67}$Ga-labeled Z00477 (SEQ. ID No. 3)-NOTA after 1 hour of reaction.
Figure 22:
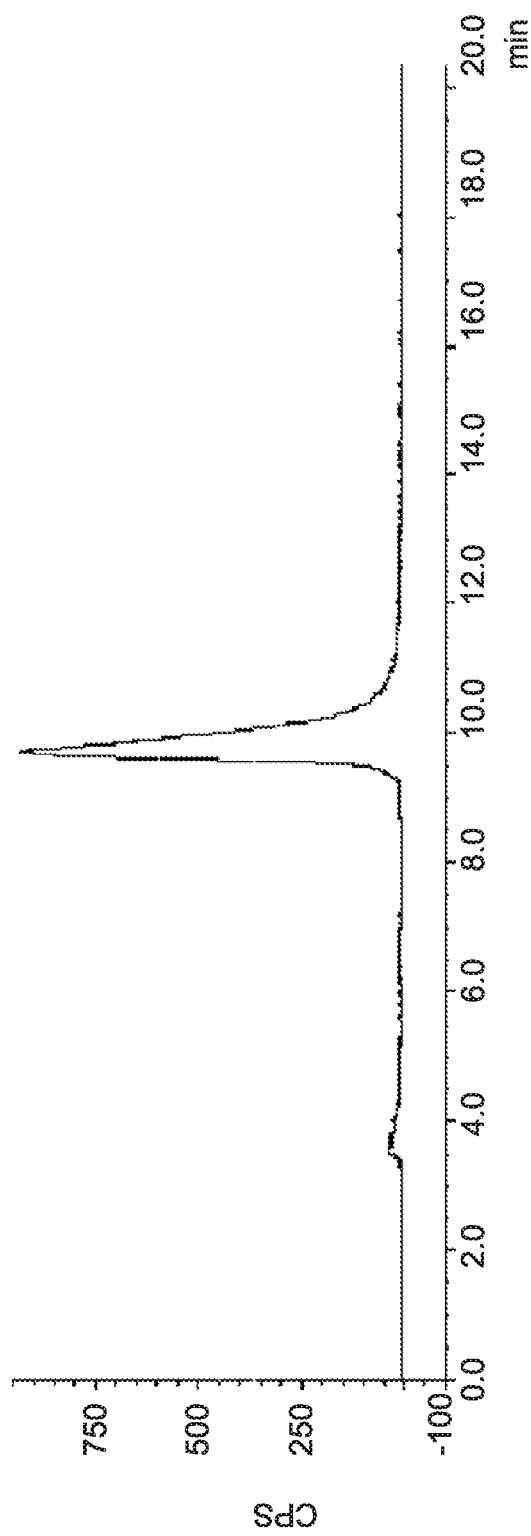
FIG. 22 is a graph of the reverse phase HPLC gamma trace for the purified $^{67}$Ga-labeled NOTA Z00477 (SEQ. ID No. 3)-NOTA polypeptide.

Radiolabeling was subsequently accomplished as follows: 25 μl HEPES solution (63 mM) was initially added to a screw top vial followed by 10 μl $^{67}$GaCl$_3$ (GE Healthcare) in 40.5 MBq of 0.04M HCl. 30 μg (MW=7506, 4.0×10$^{-9}$ mol) of the NOTA Z00477 (SEQ. ID No. 3) in 30 μl H$_2$O was then added to the reaction mixture to give a final NOTA Z00477 (SEQ. ID No. 3) concentration of 61 μM with a pH of 3.5-4.0. The reaction vial was sealed and the reaction maintained at ambient temperature. Reverse phase HPLC analysis of the crude reaction mixture determined the radiochemical purity of the $^{67}$Ga-NOTA Z00477 (SEQ. ID No. 3) was determined to be 95% by HPLC after 2 hours at room temperature. (FIG. 21) The $^{67}$Ga-NOTA Z00477 (SEQ. ID No. 3) was purified by HPLC after a reaction time of 1 day. 22 MBq of $^{67}$Ga-NOTA Z00477 (SEQ. ID No. 3) was injected onto the HPLC for the purification. 15 MBq of the $^{67}$Ga labeled product was obtained from the purification (radiochemical yield=68%). HPLC solvents were removed under vacuum to give a solution with an approximate volume of 0.5 mL. Approximately 1.45 mL of Dulbecco's phosphate buffered saline was then added to give a final solution at pH 6-6.5 with a radioactivity concentration of 7.7 MBq/mL Purified, formulated $^{67}$Ga-NOTA Z00477 (SEQ. ID No. 3) was found to be stable for at least 2 hr at room temperature. (RCP=96% by HPLC) (FIG. 22).

Analytical HPLC conditions used are as follows: A Grace Vydac C$_4$ protein 5 micron, 300 Å, 4.6×250 mm HPLC column. Solvent A=95/5 H$_2$O/MeCN in 0.05% trifluoroacetic acid (TFA) Solvent B=95/5 CH$_3$CN/H$_2$O in 0.05% TFA. HPLC gradient (Min/% B): 0/0, 4/20, 16/60, 20/100, 25/100, 26/0.

Semi-preparative HPLC conditions used are as follows: Column: Grace Vydac C4 protein 5 micron, 300 Å, 4.6×250 mm Solvent A=95/5 H$_2$O/MeCN in 0.05% trifluoroacetic acid (TFA) Solvent B=95/5 CH$_3$CN/H$_2$O in 0.05% TFA. HPLC gradient (Min/% B): 0/0, 4/20, 16/60, 20/100, 25/100, 26/0.

While only certain features of the invention have been illustrated and described herein, many modifications and changes will occur to those skilled in the art. It is, therefore, to be understood that the appended claims are intended to cover all such modifications and changes as fall within the true spirit of the invention.

---

The invention claimed is:

1. A method of imaging at least a portion of a subject comprising:
   administering a composition to the subject, wherein the composition comprises an isolated polypeptide comprising SEQ. ID No. 2 conjugated with a $^{99m}$Tc via a diaminedioxime chelator, and wherein the isolated polypeptide binds specifically to HER2; and
   imaging the subject with a SPECT device.

2. The method of claim 1, further comprising the step of: diagnosing the subject with a HER2 expressing cancer.

3. The method of claim 2, wherein the HER2 expressing cancer is breast cancer.

4. The method of claim 1, wherein the diaminedioxime chelator is cPn216.

5. The method of claim 1, wherein the $^{99m}$Tc is conjugated to the isolated polypeptide via the cPn216 chelator at the N-terminus of the isolated polypeptide.

6. The method of claim 1, further comprising the step of: monitoring delivery of the composition to the subject.

* * * * *